US011571140B1

(12) United States Patent
Bethune et al.

(10) Patent No.: US 11,571,140 B1
(45) Date of Patent: Feb. 7, 2023

(54) SYSTEMS, DEVICES, COMPONENTS AND METHODS FOR BREATH ANALYSIS

(71) Applicant: Invoy Holdings Inc., Irvine, CA (US)

(72) Inventors: Kevin Bethune, Irvine, CA (US); Zachary B. Smith, Phoenix, AZ (US); Lubna M. Ahmad, Irvine, CA (US); Connie Kim, Irvine, CA (US)

(73) Assignee: Invoy Holdings Inc., Irvine, CA (US)

( * ) Notice: Subject to any disclaimer, the term of this patent is extended or adjusted under 35 U.S.C. 154(b) by 0 days.

(21) Appl. No.: 17/477,253

(22) Filed: Sep. 16, 2021

Related U.S. Application Data

(60) Provisional application No. 63/261,098, filed on Sep. 10, 2021.

(51) Int. Cl.
*A61B 5/097* (2006.01)
*A61B 5/08* (2006.01)

(52) U.S. Cl.
CPC ............. *A61B 5/082* (2013.01); *A61B 5/097* (2013.01)

(58) Field of Classification Search
CPC ................................ A61B 5/082; A61B 5/097
See application file for complete search history.

(56) References Cited

U.S. PATENT DOCUMENTS

| | | | | |
|---|---|---|---|---|
| 3,521,643 | A * | 7/1970 | Ernest ................... | A61M 15/06 128/202.21 |
| 4,928,710 | A * | 5/1990 | Campbell ............. | B63C 11/186 128/206.29 |
| 10,285,642 | B2 | 5/2019 | Ahmad et al. | |
| 10,591,460 | B1 * | 3/2020 | Ahmad ................ | G01N 1/2214 |
| 10,782,284 | B1 | 9/2020 | Ahmad et al. | |
| 2004/0077093 | A1 * | 4/2004 | Pan ........................ | A61B 5/083 436/37 |
| 2012/0021375 | A1 * | 1/2012 | Binner .................. | A61C 17/065 433/89 |
| 2016/0220148 | A1 * | 8/2016 | Reisinger ................ | A63F 13/21 |
| 2016/0262657 | A1 | 9/2016 | Ahmad et al. | |
| 2018/0161531 | A1 | 6/2018 | Costella et al. | |
| 2019/0261891 | A1 | 8/2019 | Ahmad et al. | |

OTHER PUBLICATIONS

Medical Device Depot, Inc. "Comfit Rubber Mouthpieces." MedicalDeviceDepot.Com, Published May 12, 2015, Retrieved Oct. 20, 2021, from https://www.medicaldevicedepot.com/Comfit-Rubber-Mouthpieces-p/29-77xx.htm?1=1&CartID=0.
Vitality Medical, Inc. "Universal Mouthpiece." VitalityMedical. Com, Retrieved Oct. 20, 2021, https://www.vitalitymedical.com/hudson-rei-universal-mouthpiece.html?network=u&device=e&keyword=&campaign=14638968224&adgroup=pla-906471467643&gclid=CjwKCjw2bmLBhBREiwAz6ugozW49QXQRs8OHSDATETp1KQv8i61OY1Cf58GBsuoBIT_efxr3TBxxoCRjEQAvD_BwE.

\* cited by examiner

Primary Examiner — Andrey Shostak
(74) Attorney, Agent, or Firm — Knobbe, Martens, Olson & Bear, LLP

(57) ABSTRACT

Various systems, devices, components, and methods are disclosed for measuring the concentration of an analyte, such as acetone, in a breath sample. The disclosed devices include a breath sample analysis device having a mouthpiece configured to facilitate engagement with a user's mouth to receive a breath sample. The disclosed devices also include a breath sample capture cartridge containing an interactant that extracts the analyte from a breath sample passed through the cartridge. Also disclosed are devices for routing the breath sample through the cartridge during exhalation, and for analyzing a reaction in the cartridge to measure a concentration of the analyte.

30 Claims, 14 Drawing Sheets

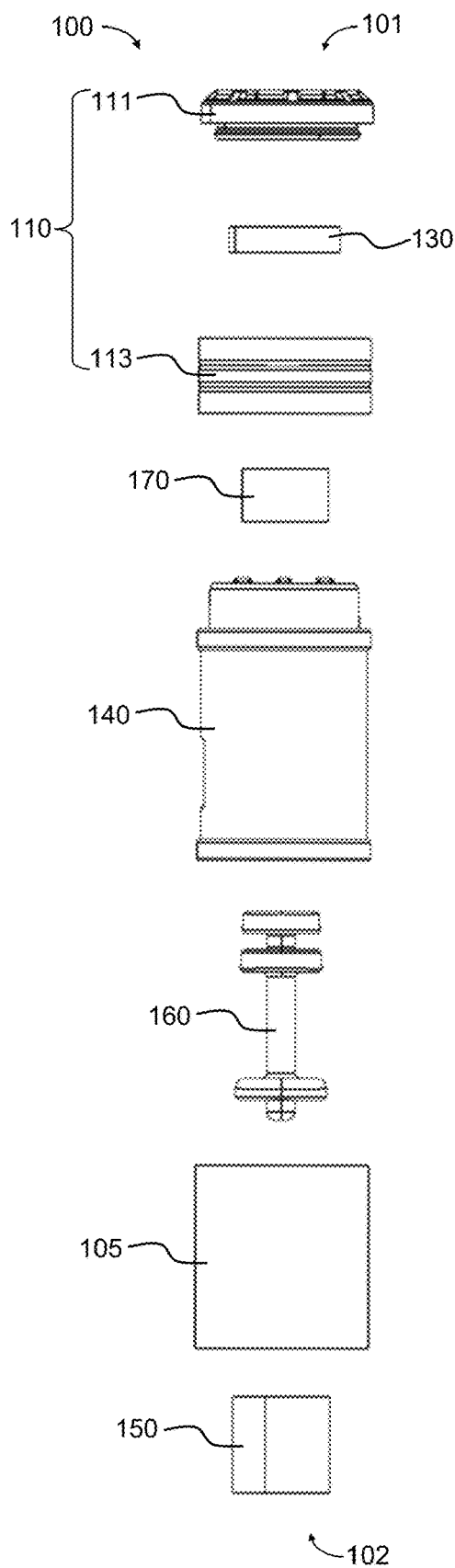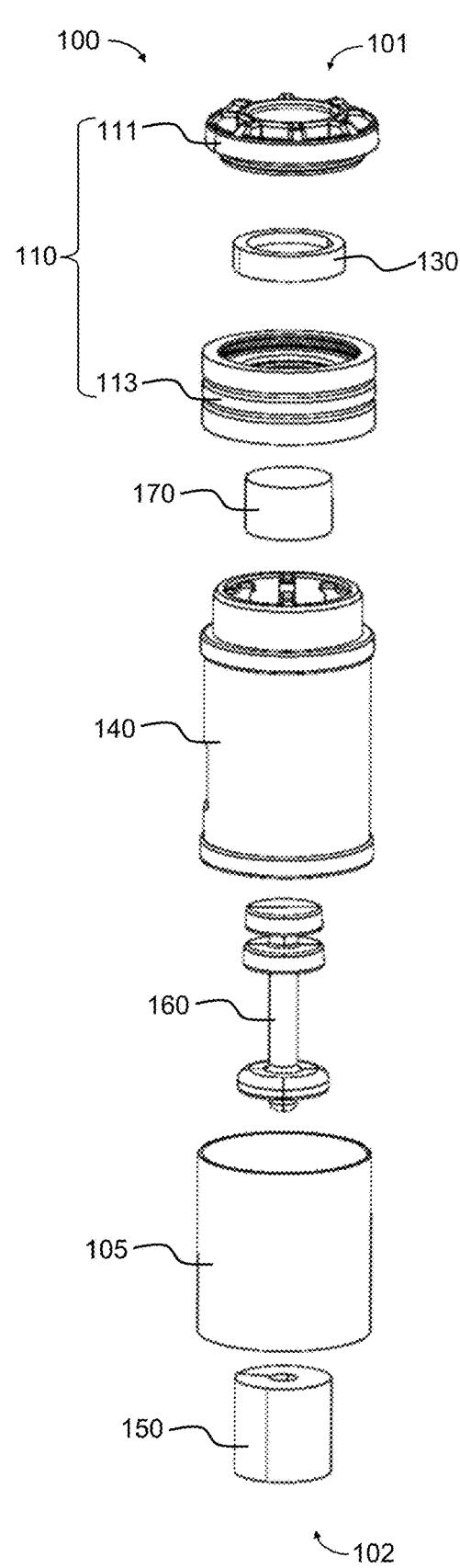
FIG. 2A  FIG. 2B

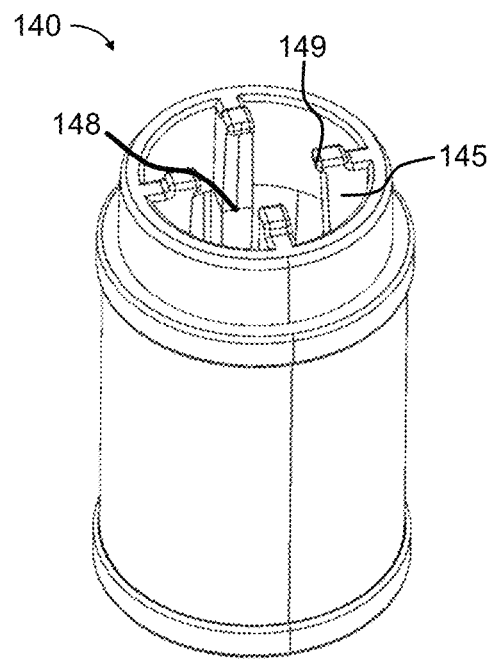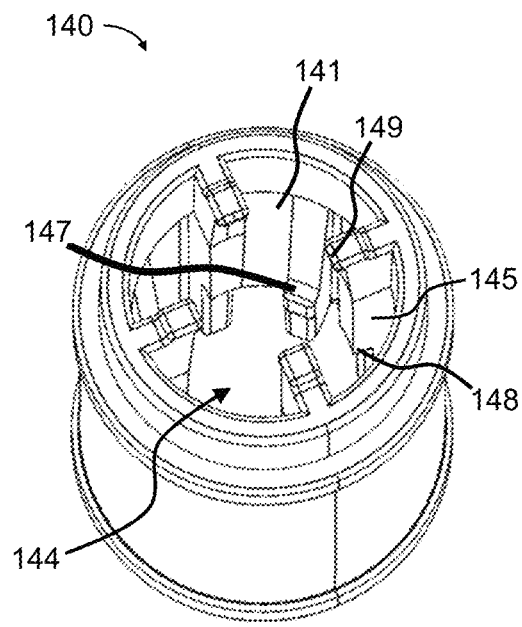
FIG. 3A　　　FIG. 3B
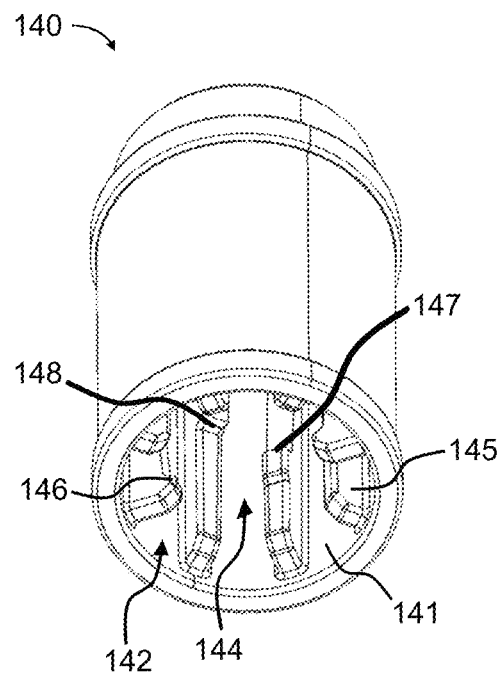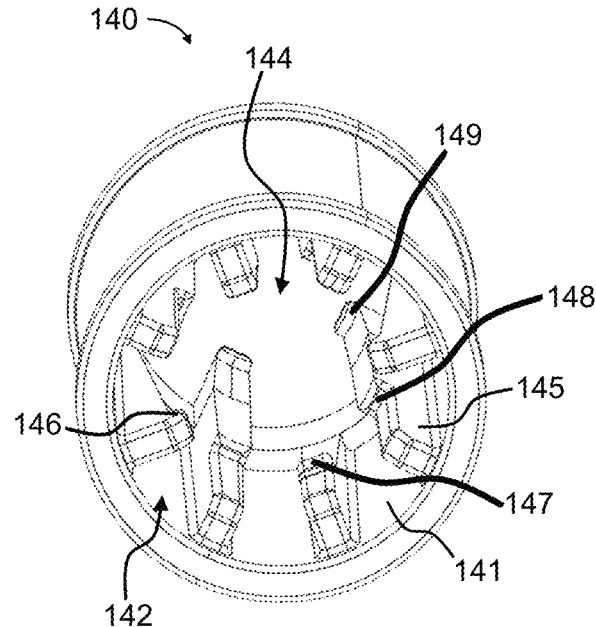
FIG. 3C　　　FIG. 3D

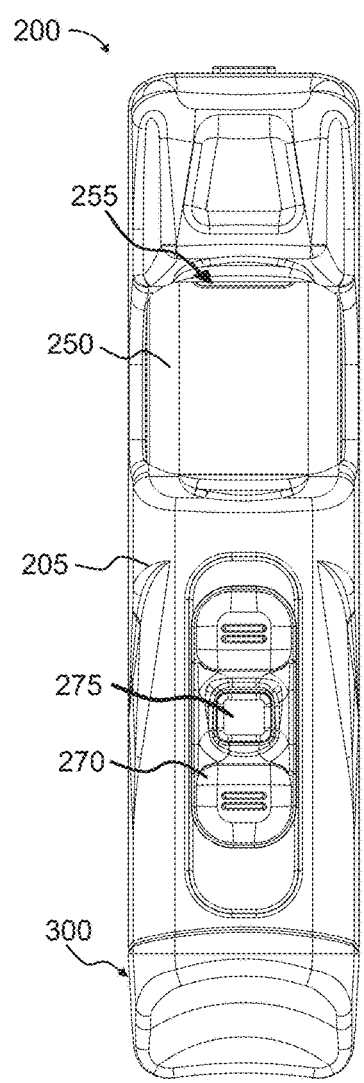
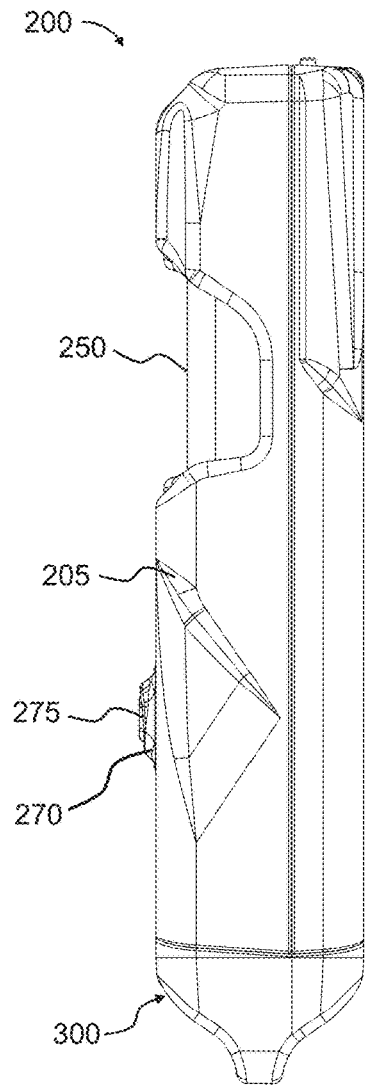
FIG. 9A  FIG. 9B
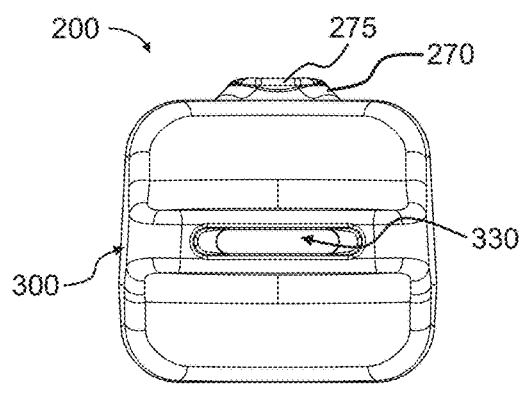
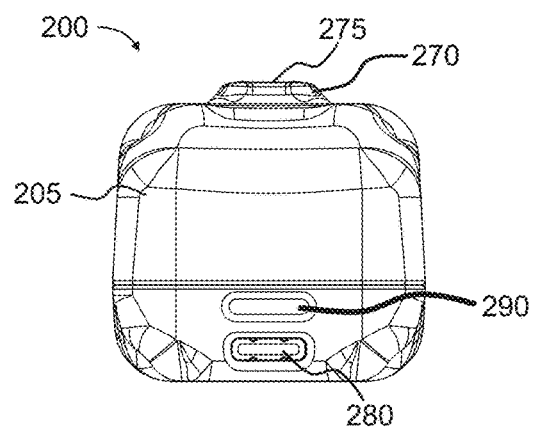
FIG. 9C  FIG. 9D

SYSTEMS, DEVICES, COMPONENTS AND METHODS FOR BREATH ANALYSIS

CROSS-REFERENCE TO RELATED APPLICATIONS

This application claims priority to U.S. Provisional Patent Application No. 63/261,098, filed Sep. 10, 2021, the entire contents of each of which are incorporated by reference herein in its entirety and for all purposes.

BACKGROUND

Field

The present disclosure relates to systems, devices, components, and methods for sensing or measuring chemical components or constituents (e.g., analytes) in the breath of a patient or "subject," and preferably endogenous analytes in breath, and correspondingly, to systems, devices, components, and methods for regulating the flow of the breath sample during the pre-measurement capture process and/or during such sensing or measurement.

Description of the Related Art

The importance or benefits of measuring the presence or concentration of chemical constituents in the body to aid in assessing a patient or subject's physiological or pathophysiological state is well known in the medical and diagnostic communities. Standard approaches to chemically-based diagnostic screening and analysis typically involve blood tests and urine tests.

Blood tests of course require that blood be drawn. Patients associate this procedure with pain, a factor that can have adverse implications for patient compliance in home-based assessments. In clinical settings, the need to draw blood typically requires trained personnel to draw the blood, carefully and properly label it, handle it and the like. It is typically necessary to transport the sample to a laboratory, often off site, for analysis. Given the logistics and economics, the lab analysis usually is carried out in bulk on large numbers of samples, thus requiring bulk handling and logistics considerations and introducing delay into the time required to obtain results. It is then typically necessary for follow-up analysis by the physician or clinician to assess the lab results and further communicate with the patient. In large part because of these logistics and delays, it is usually necessary for the patient or subject to return for a follow up visit, thus taking additional clinical time and causing additional expense.

Urine tests involve similar drawbacks. Such tests can be messy, unsanitary, and introduce issues with respect to labeling, handling and contamination avoidance. They also usually involve lab analysis, with associated delays and expense. As with blood, with urine tests it is typically necessary to transport the samples to an off-site laboratory for analysis. Given the logistics, the lab analysis usually is carried out in bulk on large numbers of samples, thus again involving delay and expense.

There are many instances in which it is desirable to sense the presence and/or quantity or concentration of an analyte in a gas. "Analyte" as the term is used herein is used broadly to mean the chemical component or constituent that is sought to be sensed using devices, components, and methods according to various aspects of the disclosure. An analyte may be or comprise an element, compound or other molecule, an ion or molecular fragment, or other substance that may be contained within a fluid. In some instances, embodiments and methods, there may be more than one analyte present, and an objective is to sense multiple analytes. "Gas" as the term is used herein also is used broadly and according to its common meaning to include not only pure gas phases but also vapors, non-liquid fluid phases, gaseous colloidal suspensions, solid phase particulate matter or liquid phase droplets entrained or suspended in gases or vapors, and the like. "Sense" and "sensing" as the terms are used herein are used broadly to mean detecting the presence of one or more analytes, or to measure the amount or concentration of the one or more analytes.

The use of breath as a source of chemical analysis can overcome many of these drawbacks. The presence of these analytes in breath and their associated correlations with physiological or pathophysiological states offer the substantial theoretical or potential benefit of providing information about the underlying or correlated physiological or pathophysiological state of the subject, in some cases enabling one to screen, diagnose and/or treat a patient or subject easily and cost effectively. Breath analysis can avoid painful invasive techniques such as with blood tests, and messy and cumbersome techniques such as urine analysis. Moreover, in many applications test results can be obtained promptly, e.g., during a single typical patient exam or office visit, and cost effectively.

As is well known in the field of pulmonology, breath, and particularly breath exhalations, comprise a range of chemical components, or analytes. An "analyte" is a chemical component or constituent that is a candidate for sensing, detection or measurement. Breath composition varies somewhat from subject to subject, and within a given subject, from time to time, depending on such factors as physical condition (e.g., weight, body composition), diet (e.g., general diet, recent intake of food, liquids, etc.), exertion level (e.g., resting metabolic rate versus under stress or exercise), and pathology (e.g., diseased state). Approximately 200 to 300 analytes can be found in human breath.

Certain breath analytes have been correlated with specific physiological or pathophysiological states. Such correlations are particularly useful for "endogenous" analytes (i.e., those that are produced by the body), as opposed to "exogenous" analytes (i.e., those that are present in breath strictly as a result of inhalation, ingestion or consumption and subsequent exhalation by the subject). Examples are set forth in Table 1.

TABLE 1

| Candidate Analyte | Illustrative Pathophysiology/Physical State |
| --- | --- |
| Acetone | Lipid metabolism (e.g., epilepsy management, nutritional monitoring, weight loss therapy, early warning of diabetic ketoacidosis), environmental monitoring, acetone toxicity, congestive heart failure, malnutrition, exercise, management of eating disorders |
| Ethanol Acetaldehyde | Alcohol toxicity, bacterial growth |
| Ammonia | Liver or renal failure, protein metabolism, dialysis monitoring, early detection of chronic kidney disease, acute kidney disease detection and management |
| Oxygen and Carbon Dioxide | Resting metabolic rate, respiratory quotient, oxygen uptake |
| Isoprene | Lung injury, cholesterol synthesis, smoking damage |

TABLE 1-continued

| Candidate Analyte | Illustrative Pathophysiology/Physical State |
|---|---|
| Pentane | Lipid peroxidation (breast cancer, transplant rejection), oxidative tissue damage, asthma, smoking damage, chronic obstructive pulmonary disease ("COPD") |
| Ethane | Smoking damage, lipid peroxidation, asthma, COPD |
| Alkanes | Lung disease, cancer metabolic markers |
| Benzene | Cancer metabolic monitors |
| Carbon-13 | *H. pylori* infection |
| Methanol | Ingestion, bacterial flora |
| Leukotrienes | Present in breath condensate, cancer markers |
| Hydrogen peroxide | Present in breath condensate |
| Isoprostane | Present in breath condensate, cancer markers |
| Peroxynitrite | Present in breath condensate |
| Cytokines | Present in breath condensate |
| Glycans | Glucose measurement, metabolic anomalies (e.g., collected from cellular debris) |
| Carbon monoxide | Inflammation in airway (asthma, bronchiectasis), lung disease |
| Chloroform | |
| Dichlorobenzene | Compromised pulmonary function |
| Trimethyl amine | Uremia |
| Dimethyl amine | Uremia |
| Diethyl amine | Intestinal bacteria |
| Methanethiol | Intestinal bacteria |
| Methylethyl-ketone | Lipid metabolism |
| O-toluidine | Cancer marker |
| Pentane sulfides | Lipid peroxidation |
| Hydrogen sulfide | Dental disease, ovulation |
| Sulfated hydrocarbon | Cirrhosis |
| Cannabis | Drug concentration |
| G-HBA | Drug testing |
| Nitric oxide | Inflammation, lung disease |
| Propane | Protein oxidation, lung disease |
| Butane | Protein oxidation, lung disease |
| Other Ketones (other than acetone) | Lipid metabolism |
| Ethyl mercaptane | Cirrhosis |
| Dimethyl sulfide | Cirrhosis |
| Dimethyl disulfide | Cirrhosis |
| Carbon disulfide | Schizophrenia |
| 3-heptanone | Propionic acidaemia |
| 7-methyl tridecane | Lung cancer |
| Nonane | Breast cancer |
| 5-methyl tridecane | Breast cancer |
| 3-methyl undecane | Breast cancer |
| 6-methyl pentadecane | Breast cancer |
| 3-methyl propanone | Breast cancer |
| 3-methyl nonadecane | Breast cancer |
| 4-methyl dodecane | Breast cancer |
| 2-methyl octane | Breast cancer |
| Trichloroethane | |
| 2-butanone | |
| Ethyl benzene | |
| Xylene (M, P, O) | |
| Styrene | |
| Tetrachloroethene | |
| Toluene | |
| Ethylene | |
| Hydrogen | |

The inherent relative advantage of breath analysis over other techniques, together with the relatively wide array of analytes and analyte correlations, illustrate that the potential benefits breath analysis offers are substantial.

Notwithstanding these potential benefits, however, with the exception of breath ethanol devices used for law enforcement, there has been a paucity of breath analyzers on the commercial market, particularly in medically-related applications. This lack of commercialization is attributable in large measure to the relatively substantial technical and practical challenges associated with the technology. Principal among them is the requirement for sensitivity. Analytes of interest, particularly endogenous analytes, often are present in extremely low concentrations, e.g., of only parts per million ("ppm") or parts per billion ("ppb"). In addition, the requirements for discrimination or selectivity is of critical concern. As noted herein above, breath typically includes a large number, sometimes hundreds, of chemical components in a complex matrix. Breath also usually has considerable moisture content. Chemical sensing regimes conducive for breath ammonia measurement, for example, are preferably sensitive to 50 ppb in the presence of 3 to 6% water vapor with 3 to 5% carbon dioxide. Successfully and reliably sensing a particular analyte in such a heterogeneous and chemically-reactive environment presents substantial challenges.

Most publicly-known breath analysis devices and methods involve using a single breath, and more specifically a single exhalation, as the breath sample to identify or measure a single analyte. The sample is collected and analyzed to determine whether the analyte is present, and in some cases, to measure its concentration. The breath analysis system introduced by Abbott Laboratories, e.g., in U.S. Pat. Nos. 4,970,172, 5,071,769, and 5,174,959, provides an illustrative example. There, Abbott used a single exhalation from a patient to detect the presence of acetone to obtain information about fat metabolism.

Notwithstanding the potential benefits of breath analysis, particularly portable breath analysis devices for home or field use, commercial offerings of such devices have been available only recently, and the accuracy and reliability in such settings have left much room for improvement. Practical breath analysis devices must operate accurately and reliably in the context of their use, e.g., in patient homes, clinics, etc., in varying environments, (temperatures, humidity, etc.), with various types of patients, over the life of the devices.

The use of multiple breaths is substantially lesser known and studied. Published reports generally have been limited to the determination of the production rate of carbon dioxide and the consumption rate of oxygen. This technique was developed due to the presence of these two analytes (oxygen and carbon dioxide) in the ambient atmosphere.

These approaches have been limited and relatively deficient, however, for example, in that the breath sample or samples are collected in bulk, so that the analyte of interest is mixed in with other constituents. This often dilutes the analyte and increases the difficulty of discriminating the desired analyte. These approaches also limit the flexibility of the breath analysis to undertake more specialized or complex analyses.

Additionally, such approaches are relatively deficient because the instrumentation used for single breath analysis usually is different from and sometimes inadequate for multiple breath analyte measurement.

Yet another challenge to breath analysis involves the fluid mechanical properties of the breath sample as it travels through the measurement device.

There is considerable advantage in providing breath analysis devices that can accurately and reliably sense or measure breath analytes in a clinical or patient home setting. Thus, there is a need for small or portable, cost effective devices and components.

In many instances, there is a need or it is desirable to make the analysis for an analyte in the field, or otherwise to make such assessment without a requirement for expensive and cumbersome support equipment such as would be available in a hospital, laboratory or test facility. It is often desirable to do so in some cases with a largely self-contained device, preferably portable, and often preferably easy to use. It also is necessary or desirable in some instances to have the capability to sense the analyte in the fluid stream in real time or near real time. In addition, and as a general matter, it is highly desirable to accomplish such sensing accurately and reliably.

The background matrix of breath presents numerous challenges to sensing systems, which necessitate complex processing steps and which further preclude system integration into a form factor suitable for portable usage by layman end-users. For example, breath contains high levels of humidity and moisture, which may interfere with the sensor or cause condensation within the portable device, amongst other concerns. Also, the flow rate or pressure of breath as it is collected from a user typically varies quite considerably. Flow rate variations are known to impact, often significantly, the response of chemical sensors. Breath, especially when directly collected from a user, is typically at or near core body temperature, which may be considerably different than the ambient temperature. Additionally, body temperature may vary from user to user or from day to day, even for a single user. Devising a breath analyzer thus is a non-trivial task, made all the more difficult to extent one tries to design a portable and field-amenable device.

Notably, the measurement of endogenous analytes in breath presents different challenges and requires different techniques and devices than the measurement of exogenous analytes. Endogenous analytes are those that are produced by the body, excluding the lumen of the gastrointestinal tract, whereas exogenous analytes are those that are present in breath as a result of the outside influence or as a result of user consumption. However, many analytes are produced endogenously and can also be exogenously introduced. For example, ammonia is produced endogenously through the metabolism of amino acids, but can also be introduced exogenously from the environment such as ammonia-containing household cleaning supplies. The term "endogenous" is used according to its common meaning within the field. Endogenous analytes are produced by natural or unnatural means within the human body, its tissues or organs, typically excluding the lumen of the gastrointestinal tract.

There are a number of significant challenges to measuring endogenous analytes in breath. Endogenous analytes typically have significantly lower concentrations in the breath, often on the order of parts per million ("ppm"), parts per billion ("ppb"), or less. Additionally, measurement of endogenous analytes requires discrimination of the analyte in a complex matrix of background gases. Instead of typical atmospheric gas composition (e.g., primarily nitrogen), exhaled breath has high humidity content and larger carbon dioxide concentration. This leads to unique challenges in chemical sensitivity, selectivity and stability. For example, chemistries conducive for breath ammonia measurement are preferably sensitive to 50 ppb in the presence of 3 to 6% water vapor with 3 to 5% carbon dioxide.

Because of the historical difficulty in even detecting endogenous breath analytes, other challenges have not been extensively investigated. Examples of such challenges include: (a) correlating the analytes to health or disease states, (b) measuring these analytes given characteristics of human exhalation, e.g., flow rate and expiratory pressure, (c) measuring these analytes sensitively and selectively, and (d) doing all these in a portable, cost effective package that can be implemented in medical or home settings.

Colorimetric devices are one method for measuring a reaction involving a breath analyte. Colorimetric approaches to endogenous breath analysis have historically been plagued with lengthy response times, and expensive components. Often such analysis has to be performed in a laboratory.

Breath analysis has also been performed with systems that use collection bags (such as gas chromatography) or systems that involve little to no flow restriction on the part of the user (such as capnography systems or alcohol breath analyzers). These solutions, however, do not address the problem of measuring low concentrations of volatile organic compounds (VOCs), such as acetone, or other analytes at ppm levels in a home or point of care environment for at least two reasons. First, using a bag is not desirable for a device that is primarily used at home, especially as sustainability becomes more of a design priority and given the obvious human factors implications. Second, systems that measure low concentrations of VOCs or other analytes typically involve biosensors or capture mechanisms that have a non-trivial level of flow resistance. For users who may have restrictions around facial muscles, making a complete seal with a breath analysis device to provide a breath sample without losing the valuable sample due to air leak between the user and device may be a challenge.

Thus, there remains a need for a breath analyzer that can measure endogenous breath components present in relatively low concentrations, such as acetone, accurately and quickly, without a long wait period for results, in addition to being inexpensive and useable by the layperson. There also remains a need for an improved interface to seal between a user and a breath analysis device to minimize or prevent air leaks during the collection of a breath sample. It is also preferable if the breath analyzer is capable of measuring multiple analytes.

The above-noted problems are not necessarily addressed by all of the disclosed embodiments. For example, some problems may be addressed by some embodiments, while other problems are addressed by other embodiments. Thus, the foregoing description should not be relied upon to limit the scope of protection.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for breath analysis.

In one aspect, a breath analysis device is provided. The breath analysis device may comprise: a breath sample collection body comprising a housing and an internal passage configured to route a breath sample within the housing for collection and/or analysis of a breath analyte; and a mouthpiece body having a proximal end, a distal end, a vertical height, a horizontal width and a horizontal length, wherein the mouthpiece body terminates at the proximal end in an upper lip surface and a lower lip surface, wherein the upper lip surface and the lower lip surface extend generally horizontally across substantially the entire horizontal width of the mouthpiece body, wherein the vertical height between the upper and lower lip surfaces is less than the vertical height of the mouthpiece body at the distal end; an inlet opening at the proximal end of the mouthpiece body, the inlet opening having a vertical height and a horizontal width, wherein the horizontal width is greater than the vertical height; and an outlet opening within the mouthpiece body, the outlet opening being in fluid communication with the internal passage of the breath sample collection body. In some embodiments, the mouthpiece body further comprises an upper transition surface extending lengthwise from the upper lip surface toward the distal end, and a lower transition surface extending lengthwise from the upper lip surface toward the distal end, and a lower transition surface extending lengthwise from the lower lip surface toward the distal end, the upper and lower transition surfaces being partially vertically inclined and extending across substantially the entire width of the mouthpiece body. In some embodiments, the upper and lower transition surfaces comprise smooth, concave surfaces extending across substantially the entire width of the mouthpiece body. In some embodiments, the upper transition surface faces in a generally proximal and upward direction and the lower transition surface faces in a generally proximal and downward direction. In some embodiments, the mouthpiece body further comprises upper side edges partially surrounding the upper transition surface and the upper lip surface and lower side edges partially surrounding the lower transition surface and the lower lip surface. In some embodiments, the mouthpiece body has a substantially constant width over substantially an entire length of the upper and lower transition surfaces. In some embodiments, the upper and lower transition surfaces are partially vertically inclined at an angle between 30 and 90 degrees relative to a horizontal plane. In some embodiments, the mouthpiece body is integrally formed with the housing. In some embodiments, the mouthpiece is removably attachable to the housing. In some embodiments, the upper lip surface and the lower lip surface are substantially smooth. In some embodiments, the upper lip surface has a generally crescent shape and the lower lip surface has a generally crescent shape. In some embodiments, the inlet opening is positioned midway along the vertical height of the mouthpiece body. In some embodiments, the inlet opening has an obround shape. In some embodiments, the horizontal width of the inlet opening is between 0.75" and 1.00". In some embodiments, the vertical height between the upper and lower lip surfaces is between 0.19" and 0.4". In some embodiments, the vertical height of the mouthpiece body at the distal end is between 0.8" and 1.50". In some embodiments, the horizontal width of the mouthpiece from the distal end and over substantially the entire length of the mouthpiece body to the proximal end is between 0.88" and 1.50". In some embodiments, the horizontal length of the mouthpiece body is between 0.63" and 1.50". In some embodiments, the mouthpiece body has a generally trapezoidal transverse cross-sectional shape.

In one aspect, a breath sample capture cartridge is provided. The breath sample capture cartridge may comprise: an outer body having a proximal end, a distal end and a longitudinal axis extending between the proximal end and the distal end; a lens at the distal end of the outer body; a porous structure proximal to the lens, the porous structure supporting an interactant; a reservoir containing a developer solution proximal to the porous structure and separated from the porous structure by a gap; and a piston proximal to the reservoir, the piston being moveable along the longitudinal axis to move the reservoir into contact with the porous structure and cause the developer solution to pass through the porous structure and come into contact with the interactant. In some embodiments, the breath sample capture cartridge further comprises a desiccant surrounding the piston. In some embodiments, the outer body comprises a lens cap including the lens and a canister secured to the lens cap. In some embodiments, the outer body is substantially cylindrical. In some embodiments, the outer body has a length between 0.25" and 1.5". In some embodiments, the breath sample capture cartridge further comprises one or more channels extending from the proximal end of the outer body and along an exterior surface of the desiccant to allow passage of a breath sample to the porous structure. In some embodiments, the one or more channels comprises a plurality of channels separated by a plurality of ribs extending radially inwardly from an inner wall of the outer body. In some embodiments, the outer body comprises one or more vents at the distal end. In some embodiments, the porous structure comprises a porous structure. In some embodiments, the interactant comprises silica beads. In some embodiments, the reservoir comprises a fibrous material. In some embodiments, the desiccant comprises a fibrous material.

BRIEF DESCRIPTION OF THE DRAWINGS

FIG. 1A shows a distal end perspective view of an embodiment of a breath sample capture cartridge. FIG. 1B shows a proximal end perspective view of the breath sample capture cartridge of FIG. 1A. FIG. 1C shows a distal end view of the breath sample cartridge of FIG. 1A. FIG. 1D shows a proximal end view of the breath sample cartridge of FIG. 1A. FIG. 1E shows a side view of the breath sample cartridge of FIG. 1A. FIG. 1F shows a cross-sectional side view of the breath sample capture cartridge of FIG. 1A.

FIGS. 2A-2B show exploded views of an embodiment of a breath sample capture cartridge.

FIGS. 3A-3H show various views of an embodiment of a canister of a breath sample capture cartridge. FIGS. 3A-3B show distal end perspective views of an embodiment of a canister of a breath sample capture cartridge. FIGS. 3C-3D show proximal end perspective views of the canister of FIGS. 3A-3B. FIG. 3E shows a distal end view of the canister of FIGS. 3A-3B. FIG. 3F shows a proximal end view of the canister of FIGS. 3A-3B. FIG. 3G shows a side view of the canister of FIGS. 3A-3B. FIG. 3H shows a cross-sectional side view of the canister of FIGS. 3A-3B.

FIG. 7A shows a proximal end top perspective view and FIG. 7B shows a distal end top perspective view.

FIG. 8A shows a proximal end top perspective view and FIG. 8B shows a distal end top perspective view.

FIGS. 9A-9G show various views of an embodiment of a breath analysis device. FIG. 9A shows a top view of an embodiment of a breath analysis device. FIG. 9B shows a side view of the breath analysis device of FIG. 9A. FIG. 9C shows a proximal end view of the breath analysis device of FIG. 9A. FIG. 9D shows a distal end view of the breath analysis device of FIG. 9A. FIG. 9E shows a cross-sectional side view of the breath analysis device of FIG. 9A without a breath sample capture cartridge installed. FIG. 9F shows a cross-sectional side view of the breath analysis device of FIG. 9A with a breath sample capture cartridge installed. FIG. 9G shows a proximal end cross-sectional perspective view of the breath analysis device of FIG. 9A without a breath sample capture cartridge installed.

FIG. 10A shows a proximal end top perspective view of an embodiment of a mouthpiece of a breath analysis device. FIG. 10B shows a proximal end bottom perspective view of the mouthpiece of FIG. 10A. FIG. 10C shows a distal end top perspective view of the mouthpiece of FIG. 10A. FIG. 10D shows a distal end bottom perspective view of the mouthpiece of FIG. 10A. FIG. 10E shows a top view of the mouthpiece of a FIG. 10A. FIG. 10F shows a bottom view of the mouthpiece of FIG. 10A. FIG. 10G shows a proximal end view of the mouthpiece of FIG. 10A. FIG. 10H shows a distal end view of the mouthpiece of FIG. 10A. FIG. 10I shows a side view of the mouthpiece of FIG. 10A. FIG. 10J shows a cross-sectional side view of the mouthpiece of FIG. 10A.

DETAILED DESCRIPTION

Figure 1A:
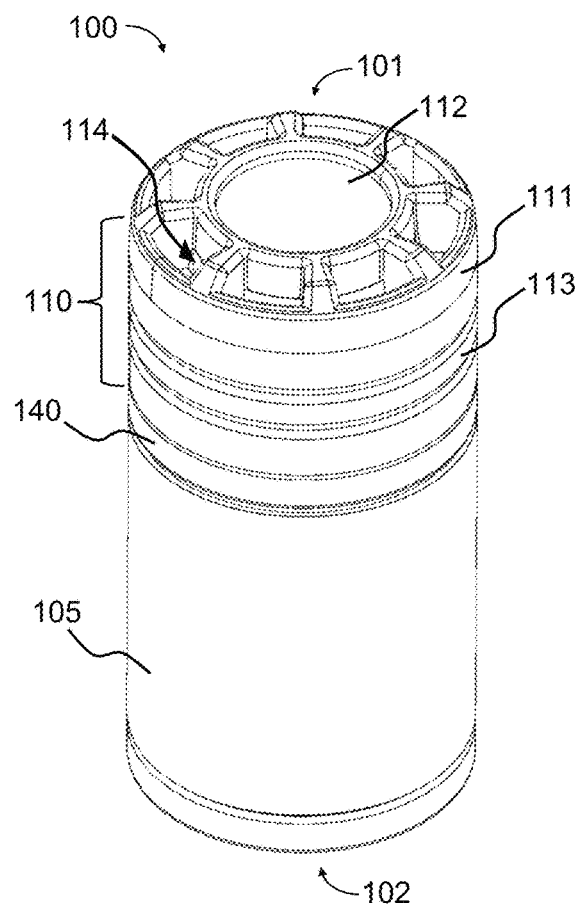
FIGS. 1A-1F show various views of an embodiment of a breath sample capture cartridge.

Embodiments of the present disclosure are directed to breath analysis systems and devices, including breath analysis devices as described with respect to FIGS. 7A-10D and breath sample capture cartridges as described with respect to FIGS. 1A-6B. Embodiments of the present disclosure are also directed to breath analysis devices in which there is a non-trivial amount of flow resistance in the flow path, such as due to the presence of a breath sample capture cartridge, including breath analysis devices as described with respect to FIGS. 7A-10D and breath sample capture cartridges as described with respect to FIGS. 1A-6B. Embodiments of the present disclosure are also directed to breath analysis devices and components that allow for a substantially leak-free seal between a user and the components of the breath analysis device, such as a mouthpiece of the breath analysis device, that require no to little activation of the user's fascial muscles to form the seal, including the breath analysis devices and components as described with respect to FIGS. 7A-10D. Embodiments of the present disclosure also encompass methods for collecting a breath sample, including the use of breath analysis devices as described with respect to FIGS. 7A-10D and breath sample capture cartridges as described with respect to FIGS. 1A-6B. Further details regarding breath analysis devices, breath sample capture cartridges and associated devices and methods that may be utilized with the embodiments of the present disclosure are described in U.S. Pat. Nos. 10,591,460 and 10,782,284, the entireties of both of which are hereby incorporated by reference and should be considered a part of this specification. Further details regarding sensors and sensor systems that may be utilized with the embodiments of the present disclosure are described in U.S. Pat. Nos. 9,689,864, 9,636,044, 9,643,186, 6,609,068, and 7,364,551, the entireties of which are hereby incorporated by reference and should be considered a part of this specification.

Breath Sample Capture Cartridge

FIGS. 1A-1F illustrate various views of an embodiment of a breath sample capture cartridge 100 that may be used to collect a fluid sample, e.g., to collect a fluid sample according to any of the number of methods disclosed herein and utilizing any of the breath analysis systems and devices described herein. The breath sample capture cartridge 100, as shown in FIGS. 1A-1F, has an outer body with a distal end 101, a proximal end 102, and a longitudinal axis 103 extending between the distal end 101 and the proximal end 102. As shown in the distal end perspective view of FIG. 1A, cartridge 100 may include a lens cap 110 with a lens cap cover 111 and a lens cap body 113 attached proximally to the lens cap cover 111. The lens cap 110 may include a lens 112 and a plurality of lens cap vents 114. The lens cap 110 may attach distally to a canister 140, e.g., fits securely on the canister 140. Canister 140 may be wrapped with a decal 105. As shown in the proximal end perspective view of FIG. 1B, canister 100 may also include a piston 160 disposed along the canister's longitudinal axis 103. Further shown, the canister 140 may include an inner wall 141 with a plurality of radially inwardly facing ribs 145 defining a plurality of channels 142 for the passage of a breath sample. While the outer body illustrated is constructed of the lens cap 110 and a separate canister 140, other embodiments may construct the outer body from a unitary structure, or from more than two separate structures. Moreover, while the canister 140 is described below as including a desiccant, other embodiments may omit the desiccant.

The breath sample capture cartridge 100 may have an outer body diameter of between about 0.25"-0.75", between about 0.275"-0.725", between about 0.3"-0.7", between about 0.325"-0.675", between about 0.35"-0.65", between about 0.40"-0.625", between about 0.425"-0.60", between about 0.45"-0.575", between about 0.475"-0.55", between about 0.475"-0.525", of about 0.50", or any other diameter that advantageously facilitates use and collection of samples as disclosed herein. The breath sample capture cartridge 100 may have a combined height, including at least both the lens cap 110 and the canister 140, of between about 0.25"-1.50", between about 0.275"-1.25", between about 0.30"-1.00", between about 0.325"-0.75", between about 0.35"-0.5", between about 0.275"-1.25", between about 0.30"-1.25", between about 0.325-1.25", between about 0.350"-1.25", between about 0.4"-1.25", between about 0.5"-1.25", between about 0.6"-1.25", between about 0.7"-1.25", between about 0.8"-1.25", between about 0.825"-1.225", between about 0.85"-1.20", between about 0.875"-1.175", between about 0.9"-1.15", between about 0.925"-1.1", between about 0.95"-1.05", 0.975"-1.025", of about 1", or any other combined height that facilitates use and collection of samples as disclosed herein.

Figure 1B:
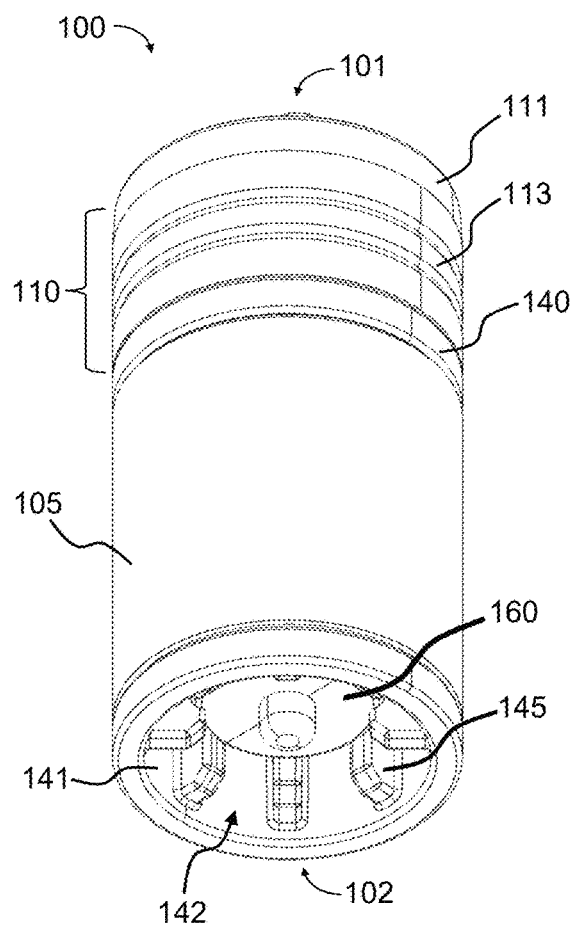
Figure 1C:
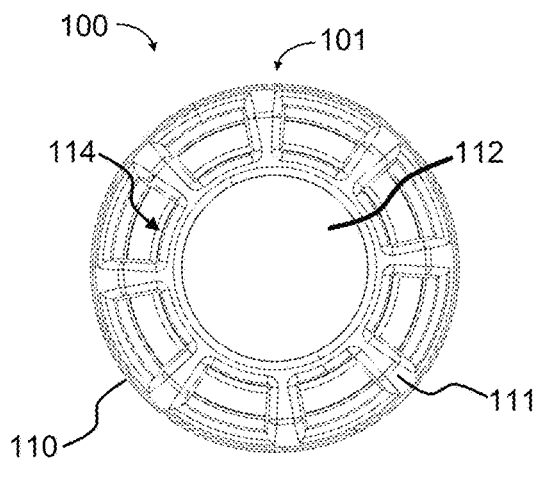
Figure 1D:
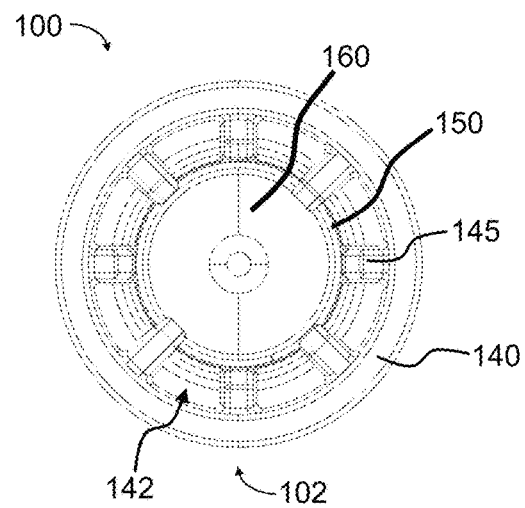

FIG. 1C illustrates a distal end view of the breath sample capture cartridge 100 of FIGS. 1A-1B, showing the lens cap 110 surrounded by several, e.g., eight, lens cap vents 114. FIG. 1D illustrates a proximal end view of the breath sample capture cartridge 100 of FIGS. 1A-1B, showing the piston 160 disposed inside the canister 140. FIG. 1D additionally shows several, e.g., eight, channels 142 extending between the inner surface 141 of the canister 140, the ribs 145 of the canister 140, and an exterior of a desiccant 150 disposed around a portion of the piston 160.

Figure 1F:
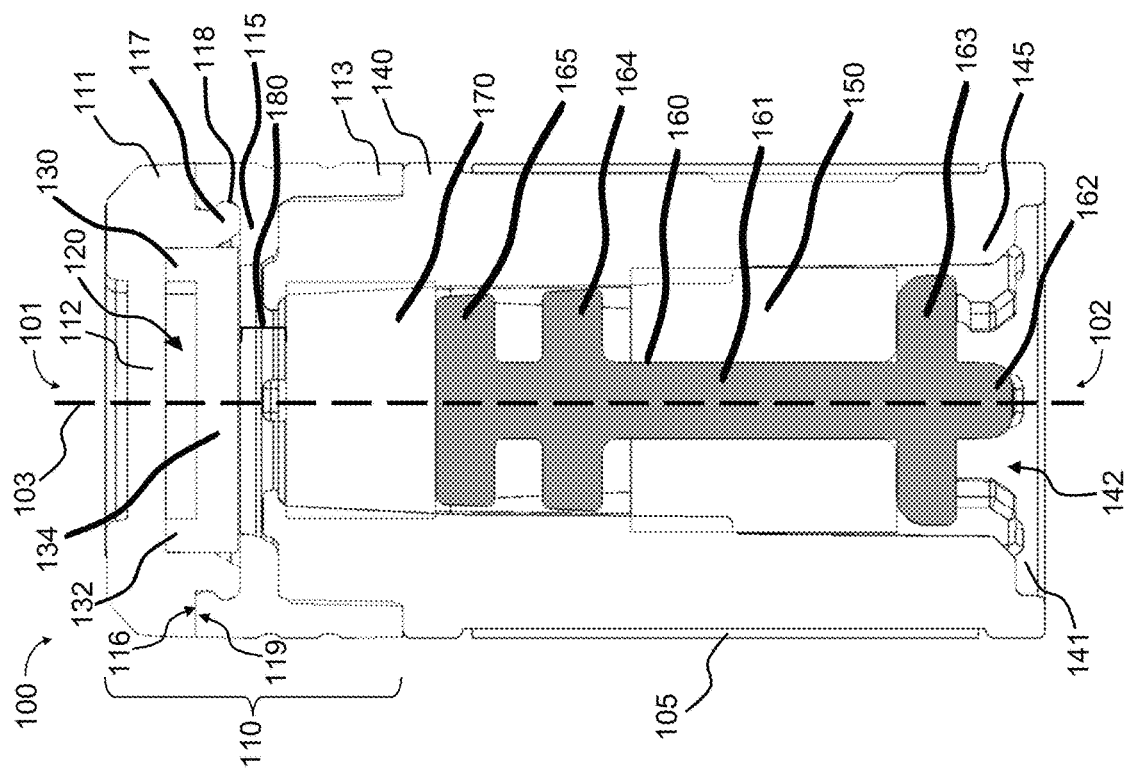
Figure 1E:
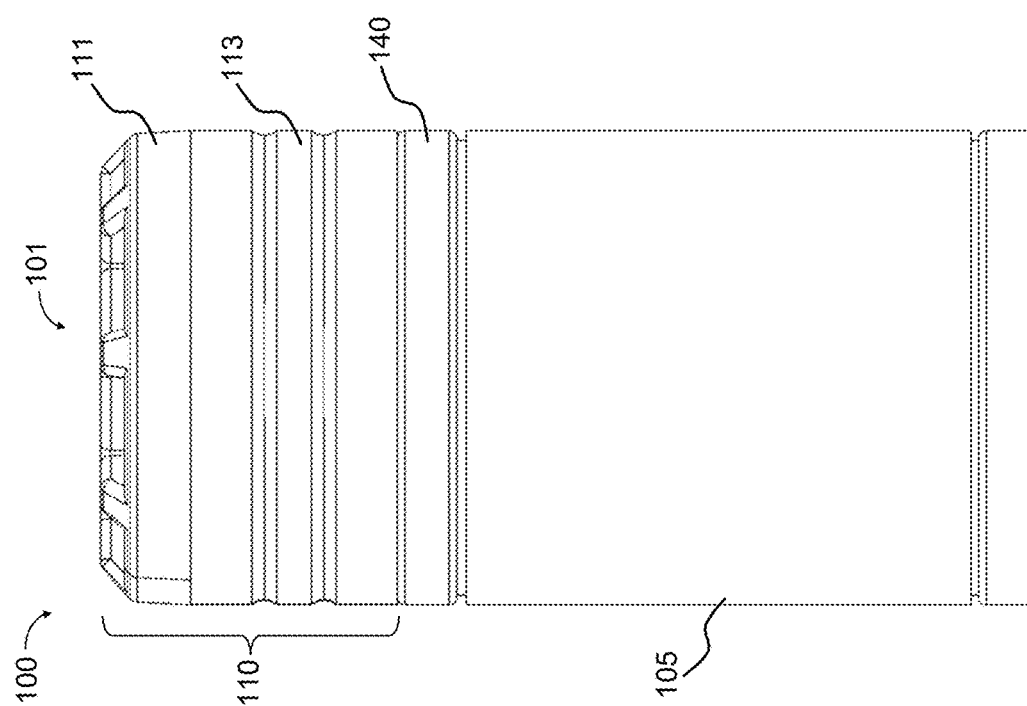

FIG. 1E illustrates a side view and FIG. 1F illustrates a cross-sectional side view of an embodiment of a breath sample cartridge 100 according to FIGS. 1A-1D. As shown in FIG. 1F, the outer body of the breath sample capture cartridge may generally include, from its distal end 101 to its proximal end 102, a lens cap 110, which as shown includes a lens cap cover 111 attached to a lens cap body 113, and a canister 140 attached to the lens cap 110 (as shown, attached to the lens cap boy 113 of the lens cap 110). Internally, the breath sample cartridge may generally include, from its distal end 101 to its proximal end 102, an interactant 120 supported by a porous structure 130 disposed inside the lens cap 110 proximal to the lens 112, a gap 180 between the porous structure 130 and a reservoir 170, the reservoir 170 containing a developer solution and disposed at the distal end of the piston 160, and the piston 160. In some embodiments, the breath sample cartridge 100 may additionally include a desiccant 150 disposed around the piston 160 proximal to the reservoir 170. The internal components of the breath sample capture cartridge may be disposed inside the lens cap 110 and the inner wall 141 and ribs 145 of the desiccant cartridge 145.

FIGS. 2A-2B illustrate exploded views of an embodiment of a breath sample capture cartridge 100, e.g., the breath sample capture cartridge 100 of FIGS. 1A-1F. The breath sample capture cartridge 100 of FIGS. 2A-2B may include a lens cap 110 including a lens cap cover 111 and a lens cap body 113, a porous structure 130, a reservoir 170, a canister 140, a piston 160, a decal 105, and a desiccant 150.

Additional detail regarding the various components of the breath sample capture cartridge 100 and interactions between them will now be discussed, in particular with reference to FIG. 1F.

The lens cap 110 may be shaped generally like a cylinder and include a lens 112 and at least one lens cap vent 114. In some embodiments, the lens cap 110 may have shapes other than a cylinder. For example, the lens cap 110 may have four sides, five sides, six sides, seven sides eight sides, or any other number of sides. Circular lens caps 110 may advantageously simplify the manufacturing process, but one of ordinary skill in the art will easily understand that a lens cap 110 having other numbers of sides may be used. The lens cap 110 may have a diameter of between about 0.25"-0.75", between about 0.275"-0.725", between about 0.3"-0.7", between about 0.325"-0.675", between about 0.35"-0.65", between about 0.40"-0.625", between about 0.425"-0.60", between about 0.45"-0.575", between about 0.475"-0.55", between about 0.475"-0.525", of about 0.50", or any other diameter that advantageously facilitates use and collection of samples as disclosed herein. The lens cap 110 may have a height of between about 0.10"-0.5", between about 0.15"-0.45", between about 0.20"-0.40", between about 0.25"-0.40", between about 0.30"-0.40", between about 0.325"-0.40", between about 0.34"-0.38", between about 0.348"-0.372", or any other height that advantageously facilitates use and collection of samples as disclosed herein.

The lens cap 110 may be a one-piece design, or it may be a two-piece design as shown in FIGS. 1A-1F and 2A-2B and include a lens cap cover 111 and a lens cap body 113. The lens cap cover 111 may have an engagement portion that couples the lens cap cover 111 to the lens cap body 113. As shown in FIG. 1F, the engagement portion may comprise a foot 117 on the lens cap cover 111 and an undercut 118 on the lens cap body 113, in the wall, e.g., the inner lateral wall, of the lens cap body 113. Other different types of engagement or coupling portions may be used, including, but not limited to, threads, friction fit, etc.

In some embodiments, the engagement portion of the lens cap 110 includes foot 117 extending proximally from the lens cap cover 111 and extending around the lens cap cover 111. In some embodiments, the foot 117 extends substantially the entire way around the lens cap cover 111, e.g., a distance of about 360°. In some embodiments, the foot 117 extends around the lens cap cover 111 less than about 360°. In some embodiments, the foot 117 comprises a plurality of distinct feet, e.g., multiple downward protrusions, rather than a single ring. In some embodiments, the foot 117 comprises a number of feet 117 between about 3-18, between about 4-16, between about 5-14, between about 6-12, and between about 7-10.

In some embodiments, the lens cap cover 111 comprises a lens cap cover mating surface 116 surrounding the foot 117. The lens cap cover mating surface 116 may be a substantially level or flat surface configured to mate with, e.g., closely mate with, a corresponding surface on the lens cap body 113.

In some embodiments, the undercut 118 of the lens cap body 113 is a mirror image or negative of the foot 117 of the lens cap cover 111. In this way, the foot 117 may "snap" into the undercut 118 of the lens cap body 113. In embodiments in which the lens cap cover 111 has more than one foot 117, the undercut 118 of the lens cap body 113 may include protrusions in the undercut 118 to index the lens cap cover 111 with respect to the lens cap body 113. In this way, exacting alignment of the lens cap cover 111 with respect to the lens cap body 113 may be reproducibly achieved.

In some embodiments, the lens cap body 113 comprises a lens cap body mating surface 119 on its distal surface. The lens cap body mating surface 119 may be a substantially level or flat surface configured to mate with, e.g., closely mate with, a corresponding surface on the lens cap cover 111. For example, the lens cap body mating surface 119 of the lens cap body 113 may be configured to mate with the lens cap cover mating surface 116 of the lens cap cover 111. In some embodiments, the lens cap body mating surface 119 may be configured to substantially sealingly mate with the lens cap cover mating surface 116 of the lens cap cover 111 when the lens cap cover 111 and the lens cap body 113 are engaged (e.g., when the foot 117 engages the undercut 118).

In some embodiments, the lens cap body 113 includes a shelf 115 extending radially inward below the undercut 118. The shelf 115 may serve as a surface against which the foot 117 of the lens cap cover 111 may abut when fully in place in the undercut 118. In some embodiments, the shelf 115 extends radially inward past the innermost surface of the foot 117. In this way, the shelf 115 may also support a porous structure 130, holding the porous structure 130 in the lens cap 110 between the lens cap cover 111 and the lens cap body 113.

FIG. 1F shows a lens cap cover 111 engaged with a lens cap body 113, such that the foot 117 has fully engaged the undercut 118 and is abutting the shelf 115. FIG. 1F additionally shows an assembled lens cap 110, including lens cap cover 111, lens cap body 113, and porous structure 130 held between the two. As can be seen, the shelf 115 of the lens cap body 113 supports the porous structure 130 and holds it securely within the lens cap cover 111.

A two-piece lens cap 110 may facilitate manufacture. In some embodiments, the lens cap 110 is manufactured by first placing a quantity of interactant 120 in a porous structure 130, which is placed on a stable and/or flat surface. A lens cap cover 111 is then placed in friction fit over the porous structure 130. As can be seen in FIG. 1F, when the porous structure 130 is fully in place within the lens cap cover 111, the proximal end of the porous structure 130 and the base of the foot 117 are substantially aligned. Therefore, the lens cap cover 111 can be installed over the porous structure 130 with some force without risking damage to the porous structure 130. The lens cap cover 111 may hold the porous structure 130 by friction, e.g., the inner lateral walls of the lens cap cover 111 may engage the outer lateral walls of the porous structure 130 such that the porous structure 130 will not easily slide out of the lens cap cover 111 once installed. After the porous structure 130 is installed in the lens cap cover 111, the lens cap cover 111 and the lens cap body 113 may be engaged. As the porous structure 130 is securely engaged with the lens cap cover 111, the construct of the lens cap cover 111 and the porous structure 130 may be introduced to the lens cap body 113 distal-side-up (as shown in FIG. 1F) or distal-side-down. The construct of the porous structure 130 and the lens cap cover 111 may simply be snapped into place within the lens cap body 113 to complete the two-piece lens cap 110.

In embodiments with a one-piece lens cap 110, the lens cap 110 may be configured to accept and hold the porous structure 130. To hold the porous structure 130, the lens cap 110 may have a retention or holding feature on its inner wall. In some embodiments, the lens cap 110 may have a continuous or partial ledge or step on its inner wall. For example, the lens cap 110 may have a continuous ramped step (e.g., ramped from the proximal end, and flat on the distal end) that is spaced a distance from the inner surface of the distal end of the lens cap 110 substantially equal to the height of the porous structure 130. Such a continuous ramped step may have a maximum width of about 0.13 mm. In other embodiments, a continuous ramped step may have a maximum width in the range of about 0.05-0.5 mm. In some embodiments, the retention or holding feature may not extend around the entirety of the lens cap 110. In some embodiments, the retention or holding feature may comprise one or more undercuts. The undercuts may be present with or without a continuous or discontinuous ramped step. The undercut may be a partial conical surface with a flat upper surface facing the distal end of the lens cap 110. Undercuts may augment or replace a continuous or partial smaller retention or holding feature. In some embodiments, the lens cap 110 has no retention or holding feature and retains the porous structure 130 through friction. In other embodiments, the porous structure 130 is held within the lens cap 110 by a distal surface of the canister 140 pushing up against the bottom of the porous structure 130 which holds the distal surface of the porous structure 130 against the inner surface of the distal end of the lens cap 110.

As shown in FIGS. 1A, 1C, and 1F, the distal end of the lens cap 110 may include a lens 112. The lens 112 may be approximately in the center of the distal end of the lens cap 110. As is discussed herein, the lens 112 may be used in an optical analysis of a sample (e.g., a photosensor measures a change in light reflectance of an interactant held behind the lens 112). For example, various embodiments of a breath analysis device described later herein may use photosensors or optical sensors to sense or detect one or more optical characteristics through the lens 112 (e.g., an optical characteristic of the interactant 120). As such, in some embodiments, the lens 112 may have a high degree of transparency. As used herein, transparency is the amount of light that passes through a barrier (e.g., the lens 112)—that is to say the total amount of light subtracting the amount of light reflected by the barrier and subtracting the amount of light absorbed by the barrier.

In some embodiments, the lens 112 has a transparency to the wavelength of light being measured (e.g., some materials have different transparencies to different wavelengths of light) of at least about 60%, at least about 65% at least about 70% at least about 75%, at least about 80%, at least about 82.5%, at least about 85%, at least about 86%, at least about 87%, at least about 88%, at least about 89%, at least about 90%, at least about 92%, at least about 93%, at least about 94%, at least about 95%, at least about 96%, at least about 97%, at least about 98%, at least about 99%, or any of amount of transmittance that advantageously facilitates analysis of a sample through the lens 112 as disclosed herein. Of course, a lens 112 having a transmission of less than about 60% may be used; however, one of ordinary skill in the art will understand that other parameters of the system may need to be adjusted to compensate for the losses due to reflectance and absorbance by the lens 112.

As shown in FIGS. 1A and 1C, the lens 112 may be circular. The lens 112 may have other shapes. For example, the lens 112 may have the same number of sides as the lens cap 110 of which it is a part (e.g., a four-sided lens cap 110 may have a four-sided lens 112, and an eight-sided lens cap 110 may have an eight-sided lens 112). In some embodiments, the lens 112 forms the entire top of the lens cap 110 (e.g., the at least one lens cap vent 114 is cut into or formed in an edge of the lens 112 that forms the top of the lens cap 110).

As shown in FIG. 1F, the lens 112 has a thickness. In some embodiments, the thickness of the lens 112 is less than the depth (distal to proximal) of the lens cap vents 114: in that way, the thickness of the lens 112 and the vertical depth of the lens cap vents 114 defines the thickness of the lens cap vents 114 (e.g., the size of the lens cap vents 114 may be defined by the width of each lens cap vent 114, the depth of each lens cap vent 114 along the longitudinal axis of cartridge 100, the radial depth of each lens cap vent 114, and the thickness of the lens 112). In some embodiments, the thickness of the lens 112 is about 0.75 mm. In some embodiments, the thickness of the lens 112 is in the range of between about 0.5-3 mm, between about 0.525-2.8 mm, between about 0.55-2.6 mm, between about 0.575-2.4 mm, between about 0.60-2.2 mm, between about 0.625-2 mm, between about 0.65-1.8 mm, between about 0.675-1.6 mm, between about 0.70-1.4 mm, between about 0.725-1.2 mm, or any other thickness that advantageously facilitates airflow through the breath sample capture cartridge 100 and/or analysis of a sample through the lens 112 as disclosed herein.

As best seen in FIG. 1A, in some embodiments, the lens cap vents 114 are cut radially into the top of the lens cap 110 deeper than the thickness of an inner side wall of the lens cap 110. In some embodiments, the lens cap vents 114 are cut into or formed in only the inner sidewall of the lens cap 110 (e.g., they do not extend into the top of the lens cap 110). In such embodiments, the top of the lens cap 110 may approximately resemble a disk set on a crenulated cylinder (e.g., in this case, the lens cap vents 114 would exit only to the "side of the lens cap 110 rather than also forming an exit on/from the top of the lens cap 110). In some embodiments, the entire top of the lens cap 110 is formed out of the lens 112. In some embodiments, the top of the lens cap 110 is a solid disc (e.g., no lens cap vent 114 is cut/formed into the top, but is rather cut/formed into the side of the lens cap 110) and the lens 112 is only in the center of the top of the lens cap 110. In some embodiments, the lens cap 110 includes an outer wall side wall that forms a ring around the lens cap vents 114. In some embodiments, each lens cap vent 114 may be formed in a generally radial fashion (e.g., the sides of each lens cap vent 114 are not parallel), as shown in FIGS. 1A and 1C. In some embodiments, each lens cap vent 114 is between about 15 and 25 degrees wide. In other embodiments, each lens cap vent 114 is less than about 5 degrees wide, less than about 10 degrees wide, less than about 15 degrees wide, less than about 20 degrees wide, less than about 25 degrees wide, less than about 30 degrees wide, less than about 40 degrees wide, less than about 50 degrees wide, less than about 60 degrees wide, less than about 70 degrees wide, less than about 80 degrees wide, less than about 90 degrees wide, or any other degree of width that advantageously facilitates sample collection as disclosed herein. In some embodiments, each lens cap vent 114 is formed as a notch in the corner of the lens cap 110 (e.g., the sides of each lens cap vent 114 are parallel, or substantially parallel).

In some embodiments each lens cap vent 114 has three sides (e.g., is a trapezoidal cut or void in the edge of the lens cap 110). In other embodiments, each lens cap vent 114 has only two sides (e.g., is a v-shaped cut or void in the edge of the lens cap 110).

In some embodiments, such as the embodiment shown in FIGS. 1A and 1C, the lens cap vents 114 are spaced evenly around the edge of the lens cap 110 (e.g., about every 45 degrees). In other embodiments, the lens cap vents 114 are grouped in patterns. In some embodiments, the lens cap vents 114 are arranged in patterns so as to facilitate spiral outflow of fluid from the interior of lens cap 110 of the breath sample capture cartridge 100. In some embodiments, the lens cap vents 114 are arranged in patterns so as to facilitate turbulent outflow of fluid from the interior of lens cap 110 of the breath sample capture cartridge 100.

In some embodiments, the lens cap vents 114 are formed at a substantially right angle with respect to the lens 112. In some embodiments, the lens cap vents 114 are cut or formed obliquely in the edge of the lens cap 110 (rather than radially) to facilitate spiral outflow of fluid from the interior of the lens cap 110 of the breath sample capture cartridge 100. In some embodiments, the lens cap vents 114 are cut or formed obliquely in the edge of the lens cap 110 (rather than radially) to facilitate turbulent outflow of fluid from the interior of the lens cap 110 of the breath sample capture cartridge 100.

In some embodiments, the lens cap vents 114 have a vertical depth (e.g., from the distal end of the lens cap 110 to the proximal end of each lens cap vent 114. Along with other features of the lens cap 110, the depth of the lens cap vents 114 may define the size of the various lens cap vents 114. In some embodiments, the depth of the lens cap vents 114 is about 0.75 mm. In some embodiments, the depth of the lens cap vents 114 is in the range of between about 0.5-3 mm, between about 0.525-2.8 mm, between about 0.55-2.6 mm, between about 0.575-2.4 mm, between about 0.60-2.2 mm, between about 0.625-2 mm, between about 0.65-1.8 mm, between about 0.675-1.6 mm, between about 0.70-1.4 mm, between about 0.725-1.2 mm, or any other depth that advantageously facilitates airflow through the breath sample capture cartridge 100 and/or analysis of a sample through the lens 112 as disclosed herein.

One of ordinary skill in the art will understand that various features of the lens cap 110 may be changed. For example, certain features of the lens cap 110 that may be changed include, but are not limited to: the size, shape, and number of the lens cap vents 114; the size, shape, and thickness of the lens 112; the diameter of the lens cap 110; and the height of the lens cap 110. The embodiment of the lens cap 110 shown in FIGS. 1A and 1C includes eight lens cap vents 114. Other numbers of vents may be used. In some embodiments, the lens cap 110 has at least 1 vent, at least 2 vents, at least 3 vents, at least 4 vents, at least 5 vents, at least 6 vents, at least 7 vents, at least 8 vents, at least 9 vents, at least 10 vents, at least 11 vents, at least 12 vents, between 12 and 20, or any number of vents that advantageously facilitates sample collection as disclosed herein.

FIGS. 1F, 2A and 2B illustrate various views of an embodiment of a porous structure 130 that may be used in conjunction with the various systems and methods disclosed herein. In some embodiments, the porous structure 130 may be configured in a bowl shape. However, reference to this element as a bowl should not limit the scope of this disclosure. The porous element or member (e.g., bowl) may have any of a number of other shapes. For example the porous structure may be a disc, a frit, a molded solid, a solid, a molded shape, a slice, etc.

The porous structure 130 may be formed to match an inner surface of a lens cap 110. For example, the porous structure 130 shown in FIG. 1F is configured to fit within a lens cap 110 having a substantially right angle where the side-wall(s) (e.g., the cylindrical side wall) of the lens cap 110 meet the distal inner surface of the lens cap 110. The porous structure 130 and the lens cap 110 may be configured to closely match (e.g., the porous structure 130 is a negative of an internal surface of the lens cap 110) so that the porous structure 130 prevents a substance or material (e.g., interactant 120) contained within the porous structure 130 from exiting the porous structure 130 and lens cap 110 through the lens cap vents 114. In some embodiments, the porous structure 130 may have rounded corners (e.g., a rounded external corner(s) matching a rounded internal corner(s) on an interior surface of the lens cap 110). While the porous structure 130 is described with reference to the accompanying figures, one of ordinary skill in the art will understand that various features of the porous structure 130 may be changed.

The porous structure 130 may have a diameter, most simply seen in FIG. 1F. The diameter of the porous structure 130 may be selected to closely match an internal diameter of the lens cap 110. It may be desirable that the porous structure 130 fit snugly, tightly, immovably, or fixedly within the lens cap 110. The diameter of the porous structure 130 may be between about 7.9-8.4 mm. In other embodiments, the diameter of the porous structure 130 is between about 4-30 mm, between about 5-25 mm, between about 6-20 mm, between about 6.5-15 mm, between about 7-10 mm, between about 7.5-9 mm, or any other diameter that advantageously facilitates use and collection of samples as disclosed herein.

The porous structure 130 may have a height, most simply seen in FIG. 1F. The porous structure's height may be from the proximal side of the porous structure base 134 to the distal side of the porous structure wall 132. In some embodiments, the height of the porous structure 130 is about 1.9-2 mm. In other embodiments, the height of the porous structure 130 is between about 0.5-3 mm, between about 0.55-2.9 mm, between about 0.6-2.8 mm, between about 0.65-2.7 mm, between about 0.7-2.6 mm, between about 0.75-2.5 mm, between about 0.8-2.4 mm, between about 0.85-2.3 mm, between about 0.9-2.2 mm, between about 0.95-2.1 mm, or any other height that advantageously facilitates use and collection of samples as disclosed herein.

The porous structure 130 may have an inner depth, most simply seen in FIG. 1F. The inner depth may be from the distal side of the porous structure base 134 to the distal side of the porous structure wall 132. In some embodiments, the inner depth is about 0.838 mm. In other embodiments, the inner depth is in the range of between about 0.5-3 mm, between about 0.525-2.8 mm, between about 0.55-2.6 mm, between about 0.575-2.4 mm, between about 0.60-2.2 mm, between about 0.625-2 mm, between about 0.65-1.8 mm, between about 0.675-1.6 mm, between about 0.70-1.4 mm, between about 0.725-1.2 mm, or any other depth that advantageously facilitates airflow through the breath sample capture cartridge 100 and/or analysis of a sample through the lens 112 as disclosed herein.

The porous structure 130 may have an inner diameter, most simply seen in FIG. 1F. In some embodiments, the inner diameter is about 6.35 mm. In other embodiments, the inner diameter is in the range of between about 5.0-8.0 mm, between about 5.5-7.5 mm, between about 5.75-7.25 mm, between about 6.0-7.0 mm, or any other diameter that advantageously facilitates use and collection of samples as disclosed herein.

As will be explained in more detail herein, the porous structure 130 may contain an interactant that collects and/or reacts with a sample and that experiences a physical change that may by assessed or measured through the lens 112. Thus, it is desirable that the porous structure 130 permit fluid flow therethrough. One of ordinary skill in the art will understand that the pore size of the porous structure 130 is dependent on at least two factors, including, but not limited to: 1) the necessary fluid flow rate through the porous structure 130 (e.g., through the breath sample capture cartridge 100) (it will be easily understood that in some embodiments the porous structure 130 is the individually greatest restriction to fluid flow through the breath sample capture cartridge 100) and 2) the particle size that must be held by the porous structure 130 (e.g., the particle size of the interactant 120 material). Stated differently, fluid flow rate through the breath sample capture cartridge 100 may be limited by the porous structure 130 and, more specifically, by the pore size of the porous structure 130. Additionally, the material contained within the porous structure 130 may have a quite small particle size, and it may be desirable to have a pore size of the porous structure 130 that prevents all or substantially all of the material contained within the porous structure 130 from passing through the porous structure base 134 or porous structure wall 132 of the porous structure 130 (e.g., it may be desirable to avoid the porous structure 130 acting like a sieve to the material it contains).

In some embodiments, the porous structure 130 has a pore size of about 130 μm. In some embodiments, the porous structure 130 has a pore size less than about 250 μm. In some embodiments, the porous structure 130 has a pore size in the range of between about 5-400 μm, between about 10-380 μm, between about 15-360 μm, between about 20-340 μm, between about 25-320 μm, between about 30-300 μm, between about 35-280 μm, between about 40-260 μm, between about 45-240 μm, between about 50-220 μm, between about 55-200 μm, between about 60-180 μm, between about 65-175 μm, between about 70-170 μm, between about 75-165 μm, between about 80-160 μm, between about 85-155 μm, between about 90-150 μm, between about 95-145 μm, between about 100-140 μm, between about 105-135 μm, between about 110-130 μm, between about 115-125 μm, or any other pore size that both strikes an advantageous balance between retaining any particle(s) within the porous structure 130 (e.g., preventing exit of the substance intended to be held within the bowl) and allowing the desired fluid flow rate through the porous structure 130.

In some embodiments, the porous structure 130 has dimensions and pore size that permits a flow rate through the porous structure 130 of between about 300-750 ml/min (e.g., the flow rate may be due to or under the pressure of a user blowing into a device holding the breath sample capture cartridge and directing the breath into and through the cartridge). In some embodiments, the porous structure 130 may permit a flow rate through the porous structure 130 of between about 4000-9000 ml/min at 3 in water back pressure. In some embodiments, the porous structure 130 is configured to permit a flow rate through the porous structure 130 of between about 50-12,000 ml/min, between about 75-11000 ml/min, between about 100-10000 ml/min, between about 125-9000 ml/min, between about 150-8000 ml/min, between about 175-7050 ml/min, between about 200-6500 ml/min, between about 225-6250 ml/min, between about 250-6000 ml/min, between about 275-5750 ml/min, between about 300-5500 ml/min, between about 325-5250 ml/min, between about 350-5000 ml/min, between about 375-4750 ml/min, between about 400-4500 ml/min, between about 425-4250 ml/min, between about 450-4000 ml/min, between about 475-3750 ml/min, between about 500-3500 ml/min, between about 525-3250 ml/min, between about 550-3000 ml/min, between about 575-2750 ml/min, between about 600-2500 ml/min, between 625-2250 ml/min, between about 650-2000 ml/min, between about 675-1750 ml/min, or any other flow rate that facilitates collection of sample from a fluid flowing through the breath sample capture cartridge 100 as disclosed herein. In some embodiments, the porous structure 130 is configured to permit a flow rate through the porous structure 130 of between about 7000-10000 ml/min.

In some embodiments, the porous structure 130 is configured to hold a material (e.g., an interactant comprising silica beads) having an average particle size of about 80 μm. In some embodiments, the porous structure 130 is configured to hold a material having an average particle size of greater than about 40 μm, greater than about 45 μm, greater than about 50 μm, greater than about 55 μm, greater than about 60 μm, greater than about 65 μm, greater than about 70 μm, greater than about 75 μm, greater than about 80 μm, greater than about 85 μm, greater than about 90 μm, greater than about 95 μm, greater than about 100 μm, greater than about 110 μm, greater than about 120 μm, greater than about 130 μm, greater than about 140 μm, greater than about 150 μm, greater than about 160 μm, greater than about 170 μm, greater than about 180 μm, greater than about 190 μm, greater than about 200 μm, greater than about 220 μm, greater than about 240 μm, greater than about 260 μm, greater than about 280 μm, greater than about 300 μm, greater than about 320 μm, greater than about 340 μm, greater than about 360 μm, greater than about 380 μm, greater than about 400, or any other size of particle that advantageously facilitates sample capture and analysis as disclosed herein. In some embodiments, the pore size of the porous structure 130 is larger (e.g., only slightly larger) than the particle size of the material to be contained within the porous structure 130. In some embodiments, the pore size of the porous structure 130 is smaller than the particle size of the material to be contained within the porous structure 130.

The material held within the porous structure 130 may be an unreactive base material or substrate, such as silica, silica gel, silica wool, glass, nitrocellulous, a sodium silicate derivate, or metal oxide, to which an interactant has been attached to cause the base material to become functionalized. The base material may be in the form of particles of various configurations (e.g., beads), although this need not be the case. In some embodiments the material contained within the porous structure 130 is an interactant 120 comprising silica. The silica may be functionalized with an amine (e.g., aminated). For example, an amine (which may later react with a sample of interest, e.g., an analyte of interest) may be bound to the surface of the silica beads or particles.

In some embodiments, the interactant 120 comprises particles of silica that are substantially round or spherical and have a particle size (e.g., an average particle size) of about 50 µm. In some embodiments the interactant 120 comprises particles of silica that have a particle size (e.g., an average particle size) of less than about 300 µm, less than about 280 µm, less than about 260 µm, less than about 240 µm, less than about 220 µm, less than about 200 µm, less than about 180 µm, less than about 160 µm, less than about 140 µm, less than about 120 µm, less than about 100 µm, less than about 90 µm, less than about 80 µm, less than about 70 µm, less than about 60 µm, less than about 50 µm, less than about 40 µm, less than about 30 µm, less than about 20 µm, or any other diameter that advantageously facilitates sample flow through the interactant 120 and interaction of the interactant 120 with the analyte of interest contained within the fluid sample. In some embodiments, the interactant 120 comprising particles of silica have a particle size (e.g., an average particle size) in the range of between about 37-53 µm, between about 53-88 µm, or between about 88-105 µm.

In some embodiments, the quantity of interactant 120 may fill the porous structure 130 more than about 50%, more than about 55%, more than about 60%, more than about 60%, more than about 70%, more than about 75%, more than about 80%, more than about 85%, more than about 90%, more than about 95%, or any other amount that facilitates capture/collection and analysis of a sample as disclosed herein.

In some embodiments, the volume of interactant 120 contained within the porous structure 130 is less than about 5 ml, less than about 4.5 ml, less than about 4 ml, less than about 3.5 ml, less than about 3 ml, less than about 2.5 ml, less than about 2 ml, less than about 1.5 ml, less than about 1.4 ml, less than about 1.3 ml, less than about 1.2 ml, less than about 1.1 ml, less than about 1 ml, less than about 0.9 ml, less than about 0.8 ml, less than about 0.7 ml, less than about 0.6 ml, less than about 0.5 ml, less than about 0.4 ml, less than about 0.3 ml, less than about 0.2 ml, less than about 0.1 ml, less than about 0.03 ml, or any other volume that facilitates capture/collection and analysis of a sample as disclosed herein.

In some embodiments, rather than using silica beads or particles, other chemistry substrates or base materials are used, such as sodium silicate derivates and/or silica/quartz wool. For example, a 4"×" strip of silica wool can be put in a solution of 1.6 ml APTES+3.2 ml propanol+3.2 ml sulfuric acid and heated to 80° C. for 2 hours and then 110° C. for 1 hour. The result is silica wool conjugated with primary amine. These substrates may have different geometries, such as planar, sheets, etc. (e.g., they may be cut or formed into disks that can be place in the porous structure 130).

Figure 3E:
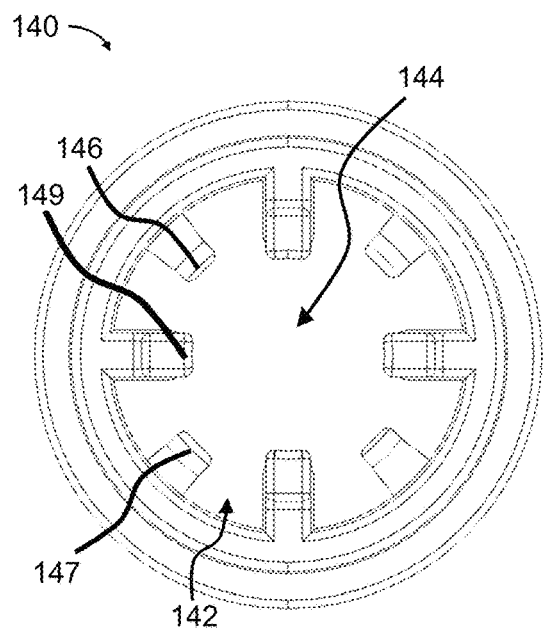
Figure 3F:
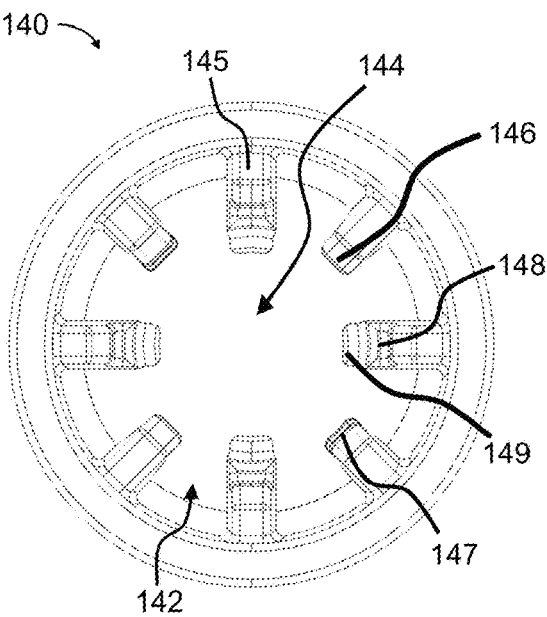
Figure 3G:
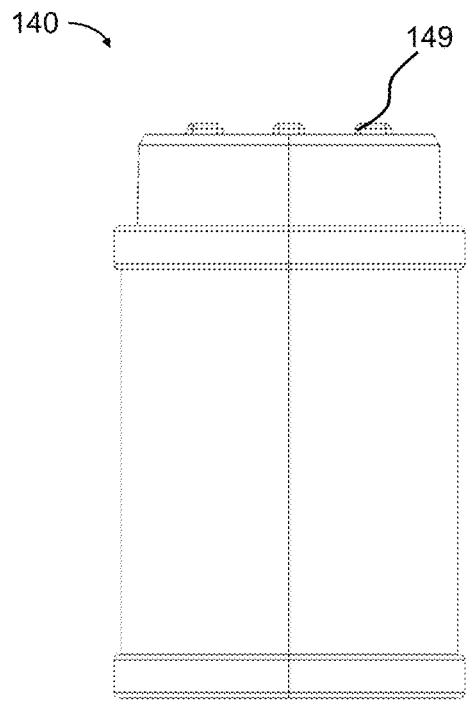
Figure 3H:
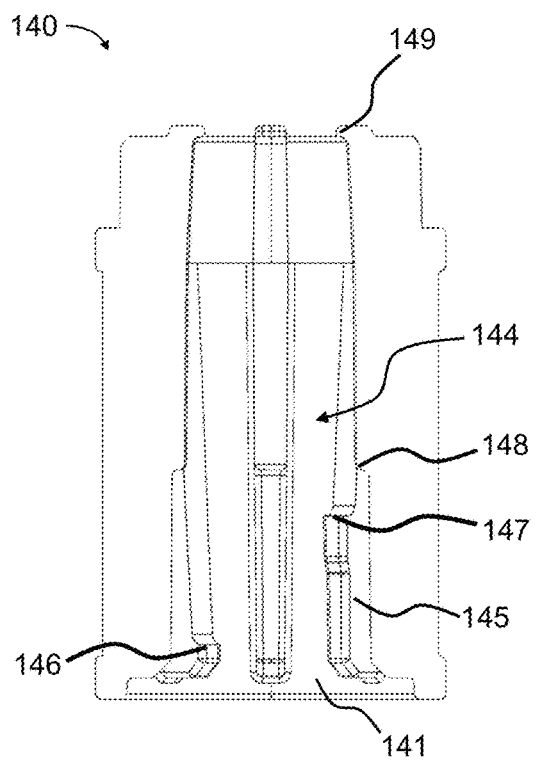

FIGS. 3A-3H show various views of an embodiment of a canister 140 of a breath sample capture cartridge 100. FIGS. 3A-3B show distal end perspective views of an embodiment of a canister 140, while FIGS. 3C-3D show proximal end perspective views of the canister of FIGS. 3A-3B. FIG. 3E shows a distal end view of the canister 140 of FIGS. 3A-3B. FIG. 3F shows a proximal end view of the canister 140 of FIGS. 3A-3B. FIG. 3G shows a side view of the canister 140 of FIGS. 3A-3B. FIG. 3H shows a cross-sectional side view of the canister 140 of FIGS. 3A-3B. As can be seen in the various views of FIGS. 3A-3H, a canister 140 may comprise a substantially cylindrical shape with a canister cavity 144 formed by the inner wall 141 of the canister 140. The canister may include one or more channels 142 separated by a plurality of ribs 145 extending radially inwardly from the inner wall 141. The one or more channels 142 may allow for the entry and passage of the sample fluid into and through the breath sample capture cartridge 100 towards the porous structure 130 and the interactant 120 it may contain. Therefore, the one or more channels 142 may advantageously have characteristics (e.g., shape, size, direction, etc.) that promote thorough and efficient mixing of the sample fluid with the interactant 120 contained within the porous structure 130. In some embodiments, such efficient mixing is achieved by inducing turbulent flow of the sample fluid. In some embodiments, the channels 142 are shaped, arranged, and oriented to increase the turbulence of fluid flow and/or mixing of the sample fluid with the interactant 120 contained in the porous structure 130. In some embodiments, the one or more channels 142 comprises a plurality of channels, e.g., 8 channels, or any other number of channels 142 that promotes fluid flow through the breath sample capture cartridge 100 and efficient mixing of the sample fluid with the interactant 120 contained in the porous structure 130.

The plurality of ribs 145 of the desiccant canister 140 may comprise various radially inward protrusions along their length, including a proximal protrusion 146, a mid-proximal protrusion 147, a mid-distal protrusion 148, and/or a distal protrusion 149. In some embodiments and as shown in FIGS. 3A-3D, the canister may include 8 ribs 145, the 8 ribs 145 including two proximal protrusions 146, two mid-proximal protrusions 146, four mid-distal protrusions 147, and four distal protrusions 148. Further as shown, a rib 145 that includes a proximal protrusion 146 or a mid-proximal protrusion 147 may not include any further protrusions along its length, while a rib 145 that contains a mid-distal protrusion 148 may also include a distal protrusion 149 along its length. A proximal protrusion 146 may comprise a ramped or curved proximal-facing end and a shelf-like distal-facing end. Likewise, a mid-proximal protrusion 147 may comprise a ramped or curved proximal-facing end and a shelf-like distal-facing end. A mid-distal protrusion 148 may comprise a ramped or curved proximal-facing end, and a distal protrusion 149 may comprise a shelf-like proximal-facing end. The various potential interactions of the ribs 145 with protrusions 146, 147, 148, and 149 with other components of the breath sample capture cartridge will be described later herein, particularly in reference to FIGS. 5A-5B. Of course, one of ordinary skill in the art will understand that various modifications to the number and orientation of the protrusions and ribs may be made compared to the embodiment shown in FIGS. 3A-3H. For example, and in some embodiments, indentations may be utilized along ribs 145 instead of protrusions.

The canister 140, in some embodiments, may have an outer body diameter of between about 0.25"-0.75", between about 0.275"-0.725", between about 0.3"-0.7", between about 0.325"-0.675", between about 0.35"-0.65", between about 0.40"-0.625", between about 0.425"-0.60", between about 0.45"-0.575", between about 0.475"-0.55", between about 0.475"-0.525", of about 0.50", or any other diameter that advantageously facilitates use and collection of samples as disclosed herein. The canister 140, in some embodiments, may have a height of about 0.8". The canister 140, in some embodiments, may have a height of between about 0.4"-1.2", between about 0.5"-1.1", between about 0.6"-1.0", between about 0.7"-0.9", between about 0.75"-0.85", or any other height that advantageously facilitates use and collection of samples as disclosed herein.

Referring back to FIG. 1F, the lens cap 110 may be fit onto the canister 140. In some embodiments, the lens cap 110 is removably attached/attachable to the cartridge canister 140. For example, the lens cap 110 may be attached to the canister 140 using threads, friction, clips, detents, springs, j-hooks, etc. In other embodiments, the lens cap 110 is fixedly attached/attachable to the canister 140. For example, the lens cap 110 may be attached to the canister 140 using epoxies, glues, welding (e.g., friction welding, and/or other types of welding), cements, locking threads, clips, co-melting plastics, etc.

In some embodiments, the canister 140 is formed out of a softer material (e.g., polymer or plastic) to facilitate the lens cap 110 slipping over the top of the canister 140. In some embodiments, an inner wall of the lens cap 110 and an outer wall of an upper portion of the canister 140 have an angle (are slightly sloped or conical) to facilitate simple and quick fitment of the lens cap 110 to the canister 140. In some embodiments, the outer wall of the canister 140 has an angle of about 92 degrees to the horizontal. In some embodiments, the outer wall of the canister 140 has an angle of less than about 100 degrees, less than about 99 degrees, less than about 98 degrees, less than about 98 degrees, less than about 97 degrees, less than about 96 degrees, less than about 95 degrees, less than about 94 degrees, less than about 93 degrees, less than about 92 degrees, less than about 91 degrees, or any other angle that facilitate application and/or removal of the lens cap 110 from the breath sample capture cartridge 100.

Referring back to FIGS. 1B, 1D, 1F, and 2A-2B, the breath sample capture cartridge may include a piston 160 disposed along its longitudinal axis 103. As shown, the piston 160 may include a longitudinal shaft 161, a proximal radial element 163, and a distal radial element 165. Further as shown, in some embodiments, piston 160 may also include a proximal shaft protrusion 162 and a mid-radial element 164. The proximal radial element 163, distal radial element 165, and mid-radial element 164 may comprise a disk-like shape, each with a proximal-facing side, a distal-facing side, and a radially outward-facing side. The radially outward-facing side of the proximal radial element 163, distal radial element 165, and mid-radial element 164 may interact with the radially inward facing ribs 145 and any protrusions 146, 147, 148, and 149 they may contain (or, in some embodiments, with any indentations along ribs 145). For example, piston 160 may slidably move along the longitudinal axis 103 of the breath sample capture cartridge 100 by interaction between the radially outward-facing side of the proximal radial element 163, distal radial element 165, and mid-radial element 164 with the radially inward facing ribs 145 and any protrusions 146, 147, 148, and 149 they may contain. In some embodiments, and to facilitate sliding movement of the piston 160 within the breath sample capture cartridge 100, the radially outward-facing sides of piston radial elements 163, 164, and 165 may be sloped or slanted relative to the longitudinal axis 103, and/or comprise rounded features.

In some embodiments, the piston 160 may have a longitudinal length of between about 0.5"-0.6", a longitudinal shaft 161 with a diameter of between about 0.05"-0.11", a proximal shaft protrusion 162 longitudinal length of between about 0.02"-0.1", and a proximal radial element 163, a mid-radial element 164, and a distal radial element 165 with diameters of between about 0.1"-0.4".

Figure 4B:
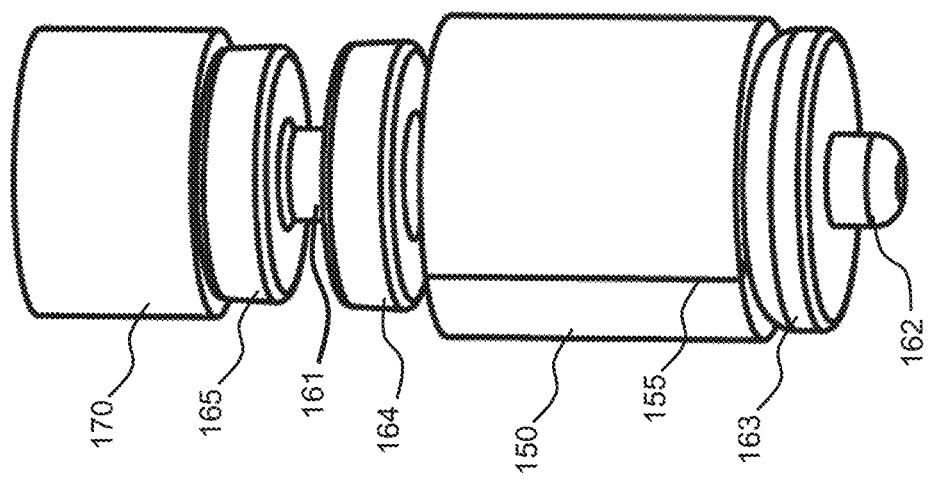
FIGS. 4A-4B show proximal end and distal end perspective views of an embodiment of a desiccant and a reservoir in relation to a piston of a breath sample capture cartridge.
Figure 4A:
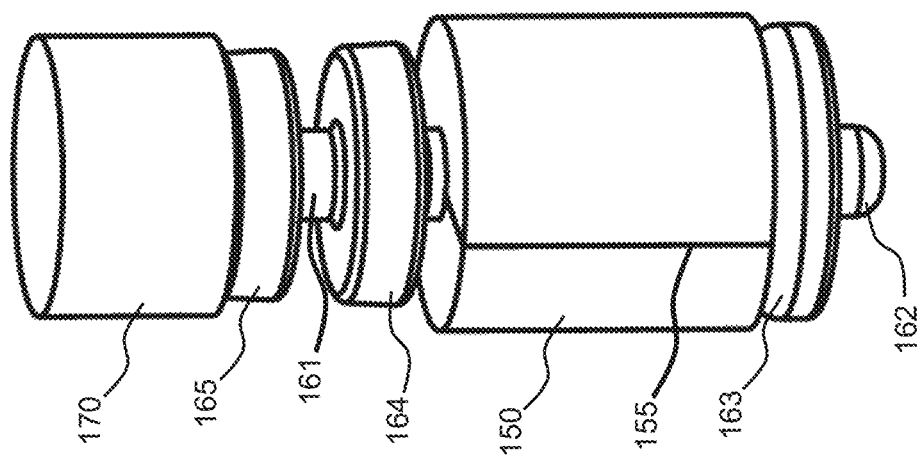

Referring back to FIGS. 1D, 1F, and 2A-2B, in some embodiments the cartridge canister 140 may contain a desiccant 150 to condition a sample-containing fluid before it exits channels 142 and enters the porous structure 130 to react with the interactant 120. As shown in FIGS. 4A-4B, the desiccant 150 may be generally cylindrically shaped with a central bore and a longitudinal slit 155 extending from the central bore through the radial thickness of the desiccant 150. Also as shown, the central bore and longitudinal slit 155 of the desiccant 150 may allow for the desiccant to be installed around the piston 160 in between a proximal radial element 163 and a mid-radial element 164 of the piston 160. In some embodiments, the desiccant 150 may comprise a fibrous and/or absorbent material, for example cotton, that can absorb moisture from the fluid sample. In some embodiments, the desiccant 150 may comprise a fibrous and/or absorbent material, for example a high release media such as PE and/or PP, that can absorb moisture from the fluid sample.

In some embodiments, desiccant 150 may have an outer diameter of between about 0.100"-0.460", between about 0.150"-0.410", between about 0.200"-0.360", between about 0.250"-0.310", between about 0.270"-0.290", between about 0.275"-0.285", of about 0.280", or any other diameter that advantageously facilitates use and collection of samples as disclosed herein. The desiccant 150, in some embodiments, may have a height of between about 0.100"-0.460", between about 0.150"-0.410", between about 0.200"-0.360", between about 0.250"-0.310", between about 0.270"-0.290", between about 0.275"-0.285", of about 0.280", or any other height that advantageously facilitates use and collection of samples as disclosed herein. The desiccant 150, in some embodiments, may have a central bore diameter of between about 0.050"-0.110", between about 0.060"-0.100", between about 0.070"-0.090", between about 0.075"-0.085", of about 0.081", or any other diameter that advantageously facilitates use and collection of samples as disclosed herein.

In some embodiments, the desiccant 150 comprises a radial dimension that allows for the desiccant 150 to be confined between ribs 145 of the canister 140. In such embodiments, canister channels 142 may be further defined by the outer radial dimension of the desiccant 150. In some embodiments, the desiccant 150 comprises a material that conforms around any ribs 145 of the canister 140 and extends radially to meet the inner wall 141 of the canister 140. In some embodiments, no desiccant may be contained in the canister 140. The absence of any desiccant in the canister 140 may advantageously promote improved transfer of fluid flow from the channels 142 to the porous structure 130, through the porous structure base 134 and into the interactant 120 contained within the porous structure 130. That is, no desiccant 150 within canister 140 may allow better fluid flow and mixing to occur in the interactant 120 because the fluid flow leaving the channels 142 is not impeded by a material or partially impeded by a material.

Referring back to FIGS. 1F and 2A-2B, in some embodiments the breath sample capture cartridge 100 may include a reservoir 170 containing a developer solution 175. The reservoir may comprise a fibrous, absorbent, and/or sponge-like material that can contain the developer solution 175 until it is compressed by the piston 160 as described herein (particularly with reference to FIGS. 6A-6B later). The reservoir 170 may, for example, be formed from a fibrous material that can serve as a high release media; for instance, the reservoir 170 may be formed as a bonded fiber reservoir containing fibers of polyethylene and polypropylene The reservoir 170 may comprise a generally cylindrical shape, with a height and a radius. The height of the reservoir 170 may be dimensioned such that it may fit in a substantially uncompressed state between the distal side of the distal radial element 165 of piston 160 and the shelf-like proximal-facing end of the distal protrusion 149 of the canister 140. In some embodiments, the height of the reservoir 170 may be about 0.157". In some embodiments, the height of the reservoir 170 may be between about 0.05"-0.25", between about 0.75"-0.225", between about 0.1"-0.2", or any other height that allows the reservoir to fit in a substantially uncompressed state between the distal side of the distal radial element 165 of piston 160 and the shelf-like proximal-facing end of the distal protrusion 149 of the canister 140. The diameter of the reservoir 170 may be dimensioned such that it may fit in a substantially uncompressed state between ribs 145 of the canister 140. In some embodiments, the reservoir 170 may have a diameter of about 0.250". In some embodiments, the reservoir 170 may have a diameter of between about 0.15"-0.350", between about 0.175"-0.325", between about 0.2"-0.3", between about 0.225"-0.275", or any other diameter that allows the reservoir to fit in a substantially uncompressed state between ribs 145 of the canister 140.

In some embodiments, the developer solution 175 contained within the reservoir 170 may be viscous. In some embodiments, the developer solution 175 is light sensitive. In some embodiments, the developer solution 175 produces a residue upon drying. In some embodiments, the developer solution 175 has a low boiling point. In some embodiments, the developer solution 175 is flammable. In some embodiments, the developer solution 175 may suffer from all of these limitations: it may be comparatively viscous, be flammable, have UV-light sensitivity, produce a crust-like residue (post dry-out), and/or have a low boiling point (which may cause pressurization or negative pressure within any rigid storage vessel). Breath sample capture cartridges 100 as disclosed herein may address each of these specialized needs.

In some embodiments, the developer solution 175 may be a mixture of methanol (which can serve as a solvent), DMSO (which can serve as a stabilizing agent), and sodium nitroprusside (SNP). Various other solvents can be used in place of methanol, such as glycerol, methyl lactate, ethyl lactate, or butyl lactate. In the case of acetone measurement, the SNP in the developer solution reacts with imines that are formed in porous structure 130 from acetone in the breath sample bonding with the interactant 120 in the porous structure 130. This reaction produces the measurable color change used to measure the quantity of extracted acetone, and thus the concentration of acetone in the breath sample. In some embodiments, developer solutions 175 containing or comprising entirely different ingredients or components may be used.

In some embodiments, the reservoir 170 disclosed herein may contain a volume of developer solution 175 of about 80 μL. In some embodiments, the reservoir 170 may contain a volume of developer solution 175 of between about 0.5-1.1 μL, between about 0.6-1.0 μL, between about 0.65-0.95 μL, between about 0.7-0.9 μL, between about 0.75-0.85 μL, or any other volume sufficient to interact with interactant 120 for analyte detection.

Referring back to FIG. 1F, in some embodiments, a breath sample capture cartridge 100 in the assembled and unused state may comprise a longitudinal gap 180 between a distal end of the reservoir 170 containing the developer solution 175 and the proximal end of the porous structure 130 (e.g., the proximal side of the porous structure base 134). The gap 180 may prevent the developer solution 175 from interacting with the interactant 120 and/or porous structure 130 before desired. In some embodiments, the gap 180 may have a longitudinal dimension of between about 0.25-4 mm or any dimension that may prevent the developer solution 175 contained within the reservoir 170 from interacting with the interactant 120 and/or porous structure 130 before desired.

In regard to the flow path of a fluid sample within a breath sample capture cartridge 100, it can be understood with reference to FIG. 1F that in at least one embodiment, the continuous flow path proceeds from the proximal end of the breath sample capture cartridge 100, into the one or more channels 142 of the canister 140, through the one or more channels 142 (and in some embodiments, also through the desiccant 150 held by the piston 160), through the porous structure base 134 of the porous structure 130, through the interactant 120, through the sides of the porous structure 130, and out through the lens cap vents 114. Of course, one of ordinary skill in the art will understand that various modifications to this flow path may be made.

Referring to FIGS. 4A-4B, shown are proximal end and distal end perspective views of an embodiment of a desiccant 150 and a reservoir 170 in relation to a piston 160 of a breath sample capture cartridge. As described herein and according to some embodiments, the desiccant 150 may be disposed surrounding the longitudinal shaft 161 of piston 160 between proximal radial element 163 and mid-radial element 164. Furthermore, the reservoir 170 may be disposed distal to the distal radial element 165 of the piston 160.

Figure 5A:
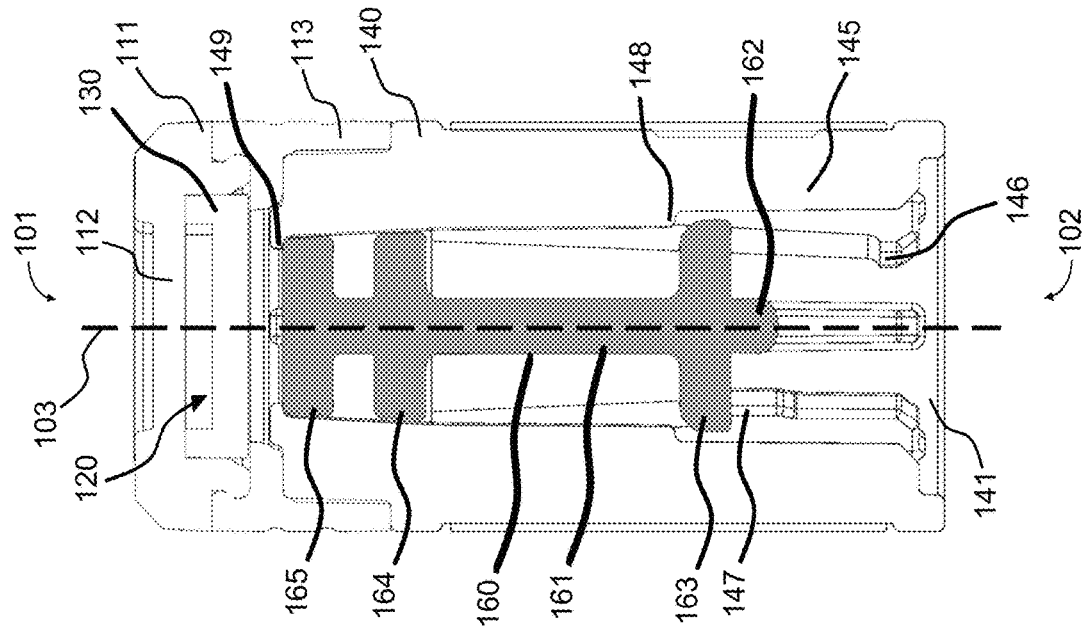
FIGS. 5A-5B show cross-sectional views of an embodiment of a breath sample capture cartridge with a piston at two positions along a longitudinal axis of the breath sample capture cartridge with a desiccant and a reservoir removed from view.
Figure 5B:
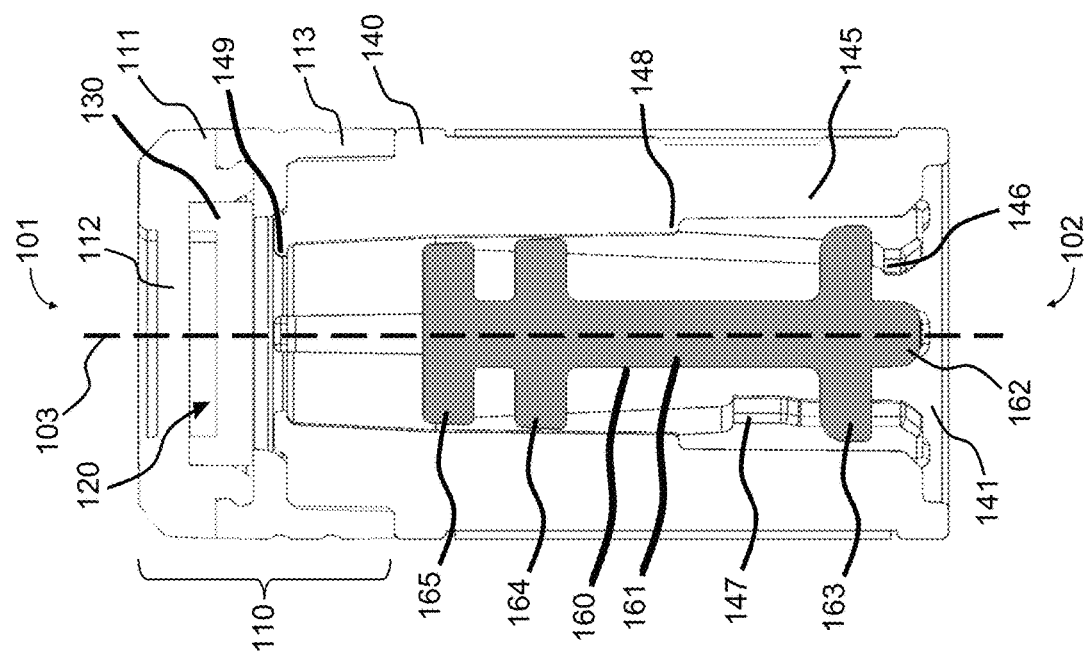

Referring to FIGS. 5A-5B, shown are cross-sectional views of an embodiment of a breath sample capture cartridge 100 with a piston 160 at two positions along a longitudinal axis 103 of the breath sample capture cartridge 100 with a desiccant 150 and a reservoir 170 removed from view. FIG. 5A shows the piston 160 in a first position, which may correspond to a breath sample capture cartridge 100 in an unused and/or new state. FIG. 5B shows the piston 160 in a second position advanced distally along longitudinal axis 103 within the breath sample capture cartridge 100, which may correspond to a breath sample capture cartridge 100 in a used and/or activated state.

As shown in FIG. 5A, in some embodiments the piston 160 may be held relatively in place in the first position by interaction of the proximal side of the proximal radial element 163 of piston 160 with the shelf-like distal-facing end of proximal protrusion 146 of a rib 145 of the canister 140 and the distal side of the proximal radial element 163 with the ramped or curved proximal-facing end of mid-proximal protrusion 147 of a rib 145. For example, the piston 160 may be prevented from translating substantially distally or proximally by the interaction of the proximal radial element 163 with protrusions 146 and 147 of ribs 145. In some embodiments (not shown), the piston 160 may be prevented from translating substantially distally or proximally by the interaction of the proximal radial element 163 with indentations in one or more ribs 145.

As shown in FIG. 5B, in the process of a user obtaining a breath sample analysis as described herein, the piston 160 may be translated distally along the longitudinal axis 103 of the breath sample capture cartridge 100 to a second position. To translate distally, a longitudinal force in the distal direction may be applied to the piston 160 at its proximal end, such as to and/or around proximal shaft protrusion 162, to cause the proximal radial element 163 of piston 160 to slide over the ramped or curved proximal-facing end of mid-proximal protrusion 147 and substantially lock into place within the breath sample capture cartridge 100. To lock in place, the proximal side of the proximal radial element 163 may interact with the shelf-like distal-facing end of mid-proximal protrusion 147. As such, once a user causes distal translation of the piston 160 within the breath sample cartridge 100, sustained force may not be required to keep the piston 160 in the second position. In some embodiments, distal translation of piston 160 within the breath sample cartridge 100 may be limited by the shelf-like proximal-facing end of distal protrusion 149 and/or the ramped or curved proximal-facing end of mid-distal protrusion 148. In some embodiments (not shown), indentations of ribs 145 may lock piston 160 in place and limit distal translation of piston 160 within the breath sample cartridge 100.

Figure 6B:
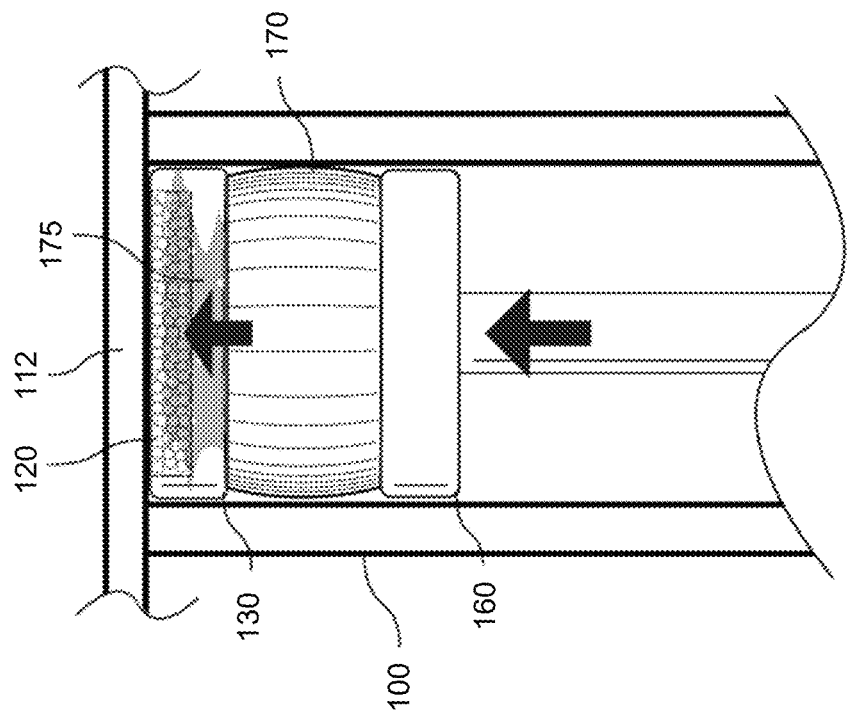
FIGS. 6A-6B show schematic views of an embodiment of a piston causing a developer solution of a reservoir to pass through a porous structure supporting an interactant and come into contact with the interactant.
Figure 6A:
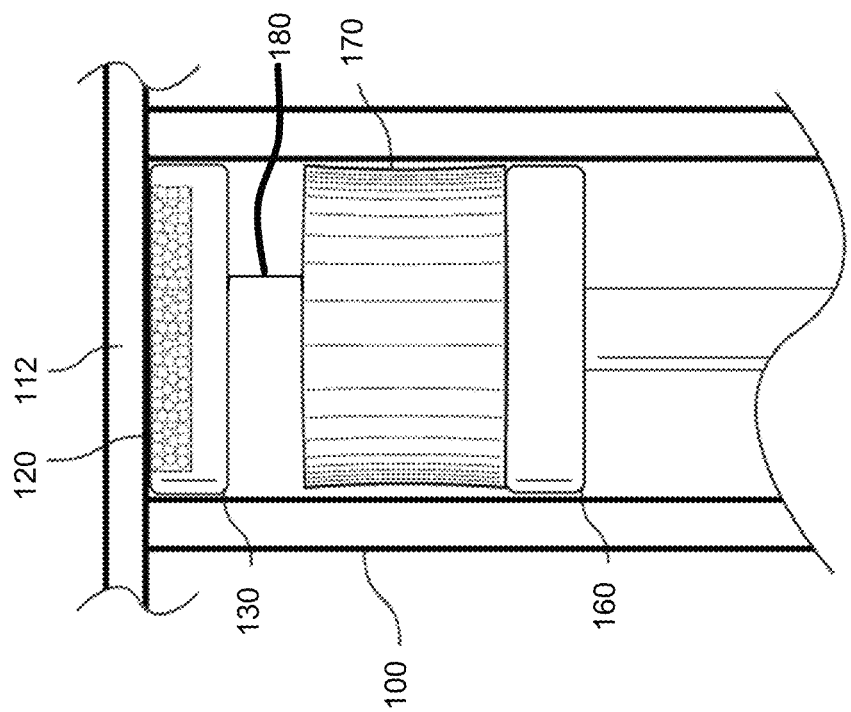

Referring to FIGS. 6A-6B, shown are schematic views of an embodiment of a piston 160 causing a developer solution 175 of a reservoir 170 to pass through a porous structure 130 supporting an interactant 120 and come into contact with the interactant 120. As shown in FIG. 6A and according to some embodiments as described herein, prior to translation of the piston 160, a gap 180 is formed between the reservoir 170 and the porous structure 130 supporting the interactant 120 (this may, for example, correspond to the first position of piston 160 as described in relation to FIGS. 5A-5B). As shown in FIG. 6B and according to some embodiments as described herein, translation of the piston 160 towards the porous structure 130 causes the reservoir 170 to come into contact with the porous structure 130, causing developer solution 175 to come into contact with the porous structure 130, and causing the developer solution 175 held by the reservoir to flow into the porous element 130 and contact interactant 120 (this may, for example, correspond to the second position of piston 160 as described in relation to FIGS. 5A-5B). In some embodiments, the flow of developer solution 175 occurs by capillary action or wicking, and does not rely on gravity to properly wet the porous structure 130 and interactant 120; thus, the porous structure 130 and interactant 120 are properly wetted regardless of the orientation of the illustrated assembly. In some embodiments, a color change or other optical change induced by the developer solution 175 is measured through the lens 112 by an optical subsystem (not shown). For example, one or more LEDs may illuminate the interactant 120 and/or porous structure 130 through the lens 112 while a photodiode measures the light reflected from the interactant 120 and/or the porous structure 130. One example of a photodiode/LED assembly and process that may be used in the various embodiments disclosed herein is disclosed in U.S. Pat. No. 10,782,284, the disclosure of which is hereby incorporated by reference and should be considered a part of this specification.

Breath Analysis Device

Figure 7A:
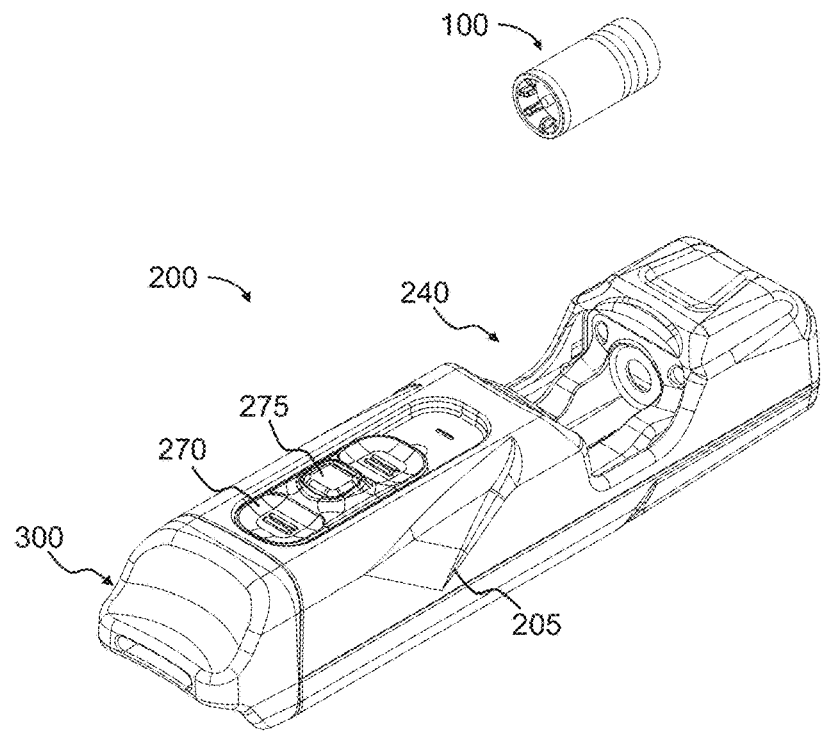
FIGS. 7A-7B show various views of an embodiment of a breath analysis device with a breath sample cartridge removed from the breath analysis device.
Figure 7B:
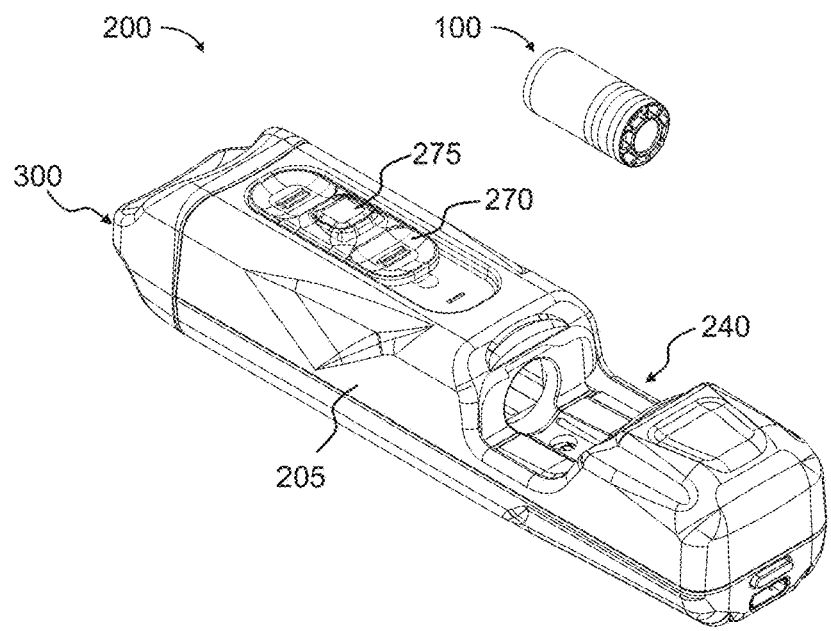
Figure 8A:
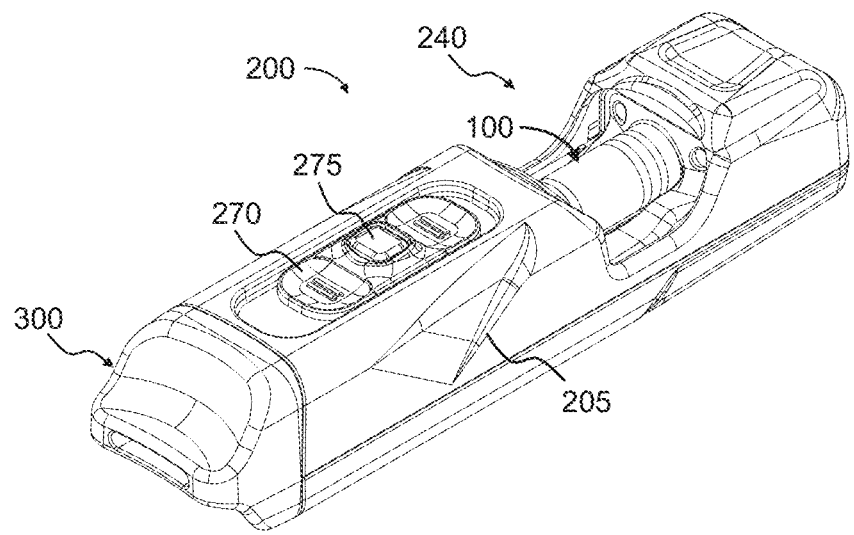
FIGS. 8A-8B show various views of an embodiment of a breath analysis device with a breath sample cartridge installed in the breath analysis device.
Figure 8B:
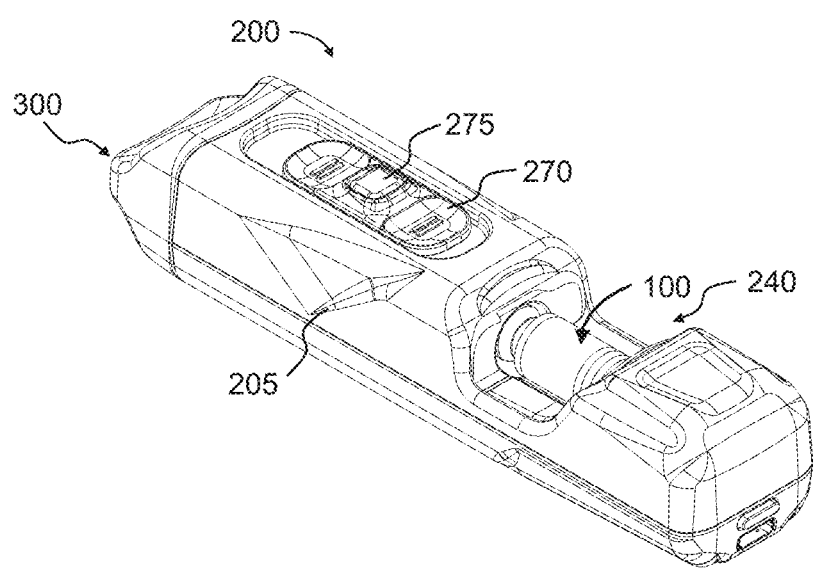

FIGS. 7A-7B, 8A-8B, and 9A-9G illustrate an embodiment of a breath analysis device 200 that may be used in conjunction with a breath sample capture cartridge 100, as disclosed herein, to collect and analyze a fluid sample (e.g., a breath sample). FIGS. 7A-7B show various views of an embodiment of a breath analysis device 200 with a breath sample cartridge 100 removed from the breath analysis device 200. FIG. 7A shows a proximal end top perspective view and FIG. 7B shows a distal end top perspective view. FIGS. 8A-8B show various views of an embodiment of a breath analysis device 200 with a breath sample cartridge 100 installed in the breath analysis device 200. FIG. 8A shows a proximal end top perspective view and FIG. 8B shows a distal end top perspective view.

As shown in FIGS. 7A-7B and 8A-8B, in some embodiments the breath analysis device 200 may comprise a mouthpiece 300 disposed at its proximal end, a housing 205, a slider 270 with a slider button 275 disposed at an upper surface of the housing 205, and a cartridge insertion window 240 disposed distal to the slider 270 for receiving the breath sample capture cartridge 100. As shown in FIGS. 7A-7B, the slider 270 is in a proximal position, which has caused a slideable door 250 (not shown) to be recessed within the housing 205 and thus exposing the cartridge insertion window 240 for receiving and/or removing of a breath sample capture cartridge 100. As shown in FIGS. 8A-8B, the breath sample cartridge 100 is installed in the breath analysis device 200 and the slider 270 is in a middle position, which has caused components of the breath analysis device 200 to form a seal (e.g., substantially air-tight seal) with the proximal end of the breath sample cartridge 100; in some embodiments, the slideable door 250 may close over the breath sample cartridge 100 when the slider 270 is its middle position, however it has been removed from view to show how the breath sample cartridge 100 may fit within the breath analysis device 200.

FIGS. 9A-9D show various views of an embodiment of a breath analysis device. FIG. 9A shows a top view of an embodiment of a breath analysis device with the slideable door 250 in its closed position. As shown, a vent 255 may be formed between the slideable door 250 and the housing 205 when the slideable door 250 is in its closed position. FIG. 9B shows a side view of the breath analysis device of FIG. 9A. FIG. 9C shows a proximal end view of the breath analysis device of FIG. 9A and further shows a mouthpiece inlet opening 330. FIG. 9D shows a distal end view of the breath analysis device of FIG. 9A and further shows a power switch 290 and a charge port 280.

Figure 9E:
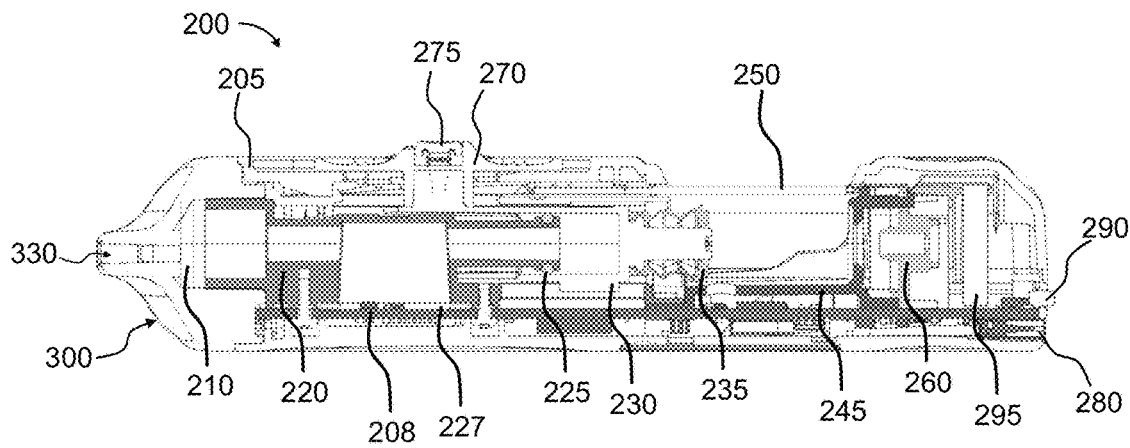
Figure 9F:
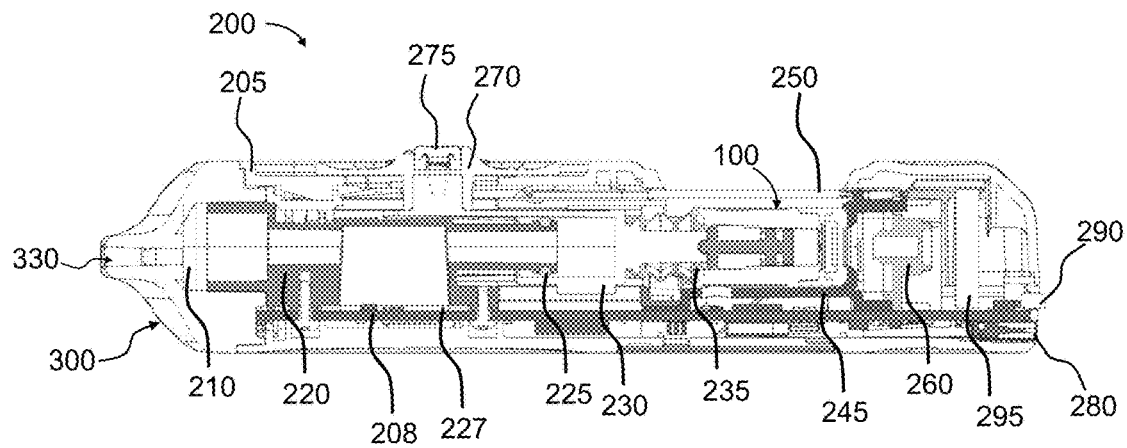
Figure 9G:
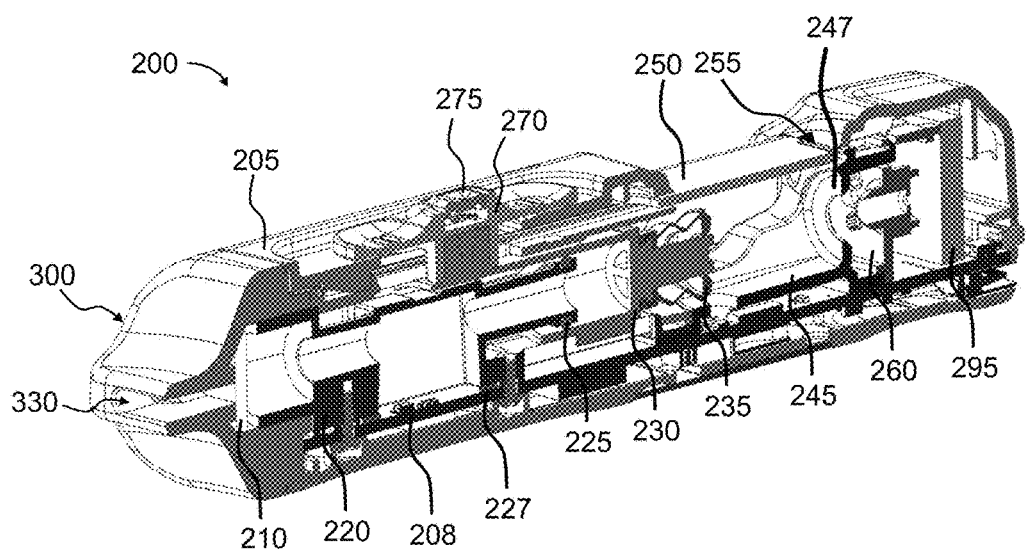

FIG. 9E shows a cross-sectional side view of the breath analysis device 200 of FIG. 9A without a breath sample capture cartridge 100 installed. FIG. 9F shows a cross-sectional side view of the breath analysis device 200 of FIG. 9A with a breath sample capture cartridge 100 installed. FIG. 9G shows a proximal end cross-sectional perspective view of the breath analysis device 200 of FIG. 9A without a breath sample capture cartridge 200 installed. According to FIGS. 9E-9G, in addition to the breath analysis device 200 components mentioned with respect to FIGS. 7A-7B, 8A-8B, and 9A-9D, the breath analysis device 200 may further comprise a filter 210, an airbox 220, an airbox sealing element 225, an airbox gasket 227, a main PCB 208, a sled 230, a cartridge gasket 235, a cradle 245, an aperture 260, LEDs 263 (not shown), a detector 265 (not shown), and a battery 295.

In some embodiments and according to FIGS. 9E-9G, the filter 210 may be disposed between the mouthpiece 300 and the airbox 220. The filter 210 may comprise a fibrous material and may capture moisture and/or debris from the sample fluid.

In some embodiments, the airbox 220 may comprise a generally cylindrical inner cavity (which may comprise one or multiple different diameters) and lie along a longitudinal axis of the breath analysis device 200. In some embodiments, a proximal end of the airbox 220 may seal (e.g., an airtight or substantially airtight seal) with the mouthpiece 300 and the inner cavity of the airbox 220 may be fluidly connected to the mouthpiece inlet opening 330. In some embodiments, a distal end of the airbox may seal (e.g., an airtight or substantially airtight seal) with the sled 230 via the airbox sealing element 225 (e.g., an O-ring). In some embodiments, the airbox 220 may comprise an open wall adjacent the main PCB 208, the open wall substantially sealed (e.g., an airtight or substantially airtight seal) via the airbox gasket 227 disposed between the airbox 220 and the main PCB 208.

In some embodiments, the main PCB 208 may comprise, within the area of the main PCB defined by airbox gasket 227 that is exposed to the internal cavity of the airbox 220, sensing elements and/or emitters, for example, flow sensors, moisture sensors, LEDs, and the like, for sensing aspects of the fluid sample and/or for signaling a user. In some embodiments, a flow sensor may detect that a gas-tight seal is not made between the breath analysis device 200 and the breath capture sample cartridge 100 and prevent a test and/or fluid sample from being taken. In some embodiments, the main PCB 208 may comprise a processor. In some embodiments, the main PCB 208 may comprise a controller. In some embodiments, the main PCB 208 may receive power from battery 295. In some embodiments, the main PCB 208 may comprise a wireless transceiver for communicating wirelessly with other electronic devices, such as a cell phone, computer, and/or servers, via a wireless network and/or a low energy RF connection (e.g., Bluetooth communication). In some embodiments, the main PCB 208 may comprise a speaker and/or a motor configured to provide auditory and/or haptic signals to a user. In some embodiments, the main PCB 208 may comprise sensor circuitry and/or components for analyzing a breath sample capture cartridge 100. In some embodiments, elements of the main PCB 208 may be in communication with one another. In some embodiments, the breath analysis device 200 may further comprise a daughter PCB, which may have all or some of the components of the main PCB 208 and may be in electrical communication with the main PCB 208.

In some embodiments, the sled 230 may comprise a generally longitudinal structure that may translate proximally and distally within the breath analysis device 200. In some embodiments, the sled 230 may translate proximally and distally within the breath analysis device 200 via proximal and distal movement of the slider 270. In some embodiments, the sled 230 may translate further distally within the breath analysis device 200 via proximal and distal movement of the slider 270 in combination with the slider button 275 being pressed inward towards the longitudinal axis of the breath analysis device 200; for example, this further distal translation may allow for distal longitudinal force to be transferred to the breath sample capture cartridge 100 and/or components thereof (e.g., the piston 160). In some embodiments, the sled 230 may comprise an inner cavity fluidly connected to the inner cavity of the airbox 220. In some embodiments, a distal end of the sled 230 may be configured to interact with the proximal end of a breath sample capture cartridge 100. In some embodiments, the distal end of the sled 230 may be configured to engage the proximal shaft protrusion 162 of piston 160 of the breath sample capture cartridge 100; such engagement may retain the breath sample capture cartridge 100 in place within the cradle 245 and allow for the transmission of longitudinal force from the slider 270 to the piston 160. In some embodiments, a distal section of the sled 230 may be surrounded by the cartridge gasket 235, and the inner cavity of the sled 230 may be in fluid communication with an internal cavity of the cartridge gasket 235. In some embodiments, the distal section of the sled 230 may align or substantially align longitudinally with the longitudinal axis 103 of the breath sample capture cartridge 100.

In some embodiments, the cartridge gasket 235 may be a generally flexible, collapsible, and tubular structure with an internal cavity as mentioned above. In some embodiments, the cartridge gasket 235 may comprise an elastomeric and bellowed structure. In some embodiments, the cartridge gasket 235 may, at its proximal end, seal (e.g., an airtight or substantially airtight seal) around and/or against the distal section of the sled 230, thus creating fluid communication between the internal cavity of the cartridge gasket 235 and the internal cavity of the sled 235. In some embodiments, the cartridge gasket 235 may, at its distal end, seal (e.g., an airtight or substantially airtight seal) with the proximal end of the breath sample capture cartridge 100. In some embodiments, via a seal between the distal end of the cartridge gasket 235 and the proximal end of the breath sample capture cartridge 100, the internal cavity of the cartridge gasket 235 may be in fluid communication with the one or more channels 142 of the breath sample capture cartridge 100.

In some embodiments, the cradle 245 may be disposed generally distal to the sled 230 and comprise a surface for receiving the breath sample capture cartridge 100. In some embodiments, a distal portion of the surface of the cradle 245 may comprise distally inclining wings that create a partially cylindrically-shaped surface of the cradle 245 and may support the breath sample capture cartridge 100 once installed. In some embodiments, a distal end of the cradle 245 may comprise a recess 247 that can receive the distal end of the breath sample capture cartridge 100. In some embodiments, the recess 247 may prevent the breath sample capture cartridge 100 from being installed incorrectly. In some embodiments, the recess 247 may prevent distal translation of the breath sample capture cartridge 100 when distal longitudinal force is applied to the proximal end of the breath sample capture cartridge 100 and/or components of the breath sample capture cartridge 100 (e.g., piston 160). In some embodiments, the surface of the cradle 245 may comprise features that can prevent the breath sample capture cartridge 100 from being installed incorrectly. For example, the surface of the cradle 245 may comprise features that can prevent the breath sample capture cartridge 100 from fully seating into the cradle 245 if not installed correctly (e.g., installed backwards) and prevent closure of the slideable door 250 (which, if not closed, may not allow the breath sample device 200 to start a test and/or receive a fluid sample). In some embodiments, the cartridge insertion window 240 is disposed above the cradle 245. In some embodiments, the cradle 245 containing the breath sample capture cartridge 100 (e.g., after the breath sample capture cartridge 100 was placed in through the cartridge insertion window 240) may have dimensions, e.g., height, width, and/or depth, slightly larger than the breath sample capture cartridge 100. In some embodiments, at least one of the height, width, or depth, is larger than the corresponding dimension of the breath sample capture cartridge 100 by at least about 101%, at least about 102%, at least about 103%, at least about 104%, at least about 105%, at least about 106%, at least about 107%, at least about 108%, at least about 109%, at least about 110%, at least about 112.5%, at least about 115%, at least about 117.5%, at least about 120%, or any other increase in size that advantageously facilitations acceptance and temporary retention of a breath sample capture cartridge 100 as disclosed herein.

In some embodiments, the aperture 260 may be disposed distal to the cradle 245 and thus adjacent to lens 112 of the breath sample capture cartridge 100 when installed in the breath analysis device 200. Details of the aperture 260, LEDs 263 (not shown), and detector 265 (e.g. a photodiode, not shown) may be as described in U.S. Pat. No. 10,782,284, the disclosure of which is already incorporated by reference herein and should be considered a part of this specification. In some embodiments, the detector 265 (e.g., photodiode) may be programmed to prevent a test and/or a fluid sample from being taken if it detects too much light caused from an open slideable door 250.

Figure 10A:
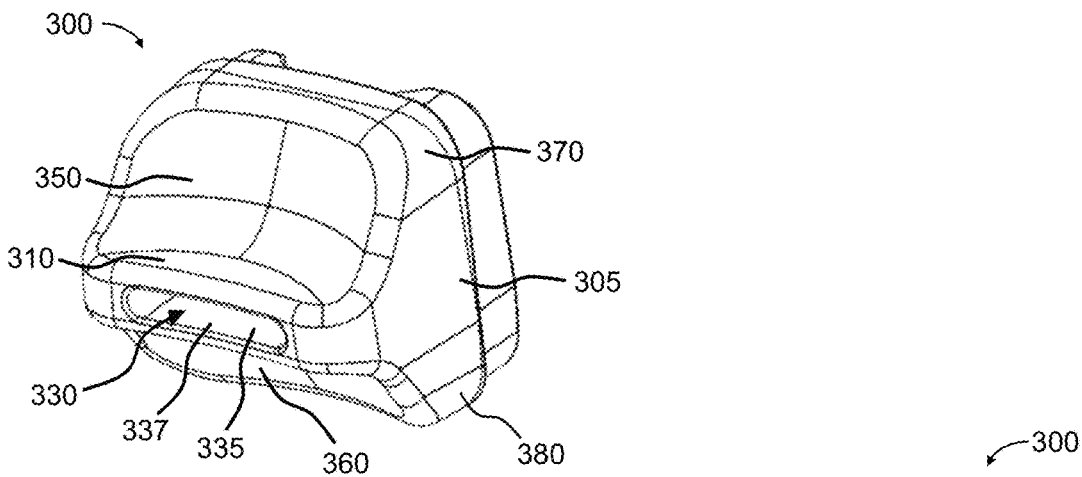
FIGS. 10A-10J show various views of an embodiment of a mouthpiece of a breath analysis device.
Figure 10B:
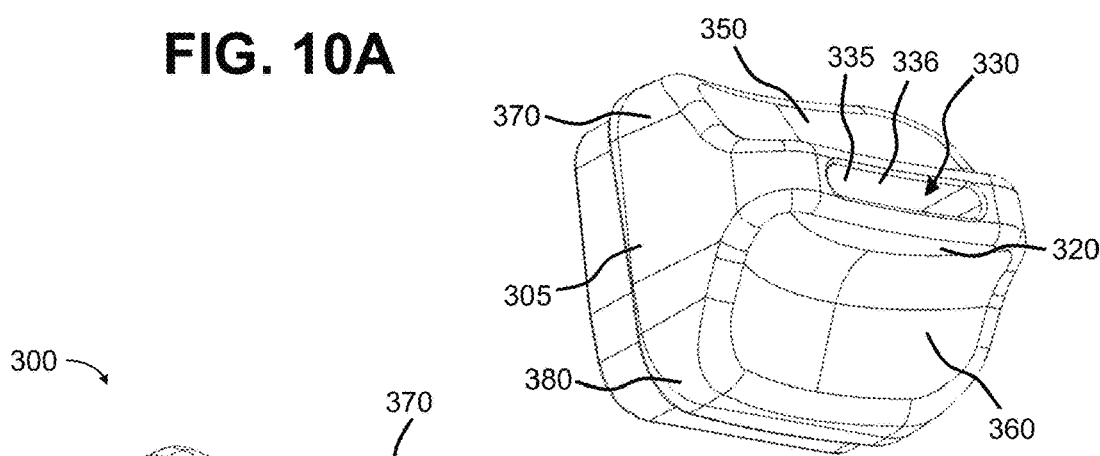
Figure 10C:
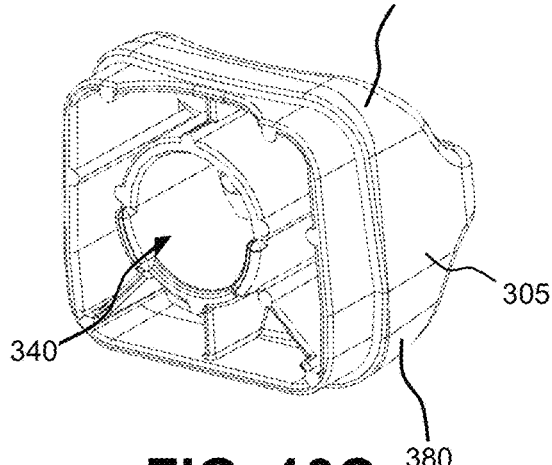
Figure 10D:
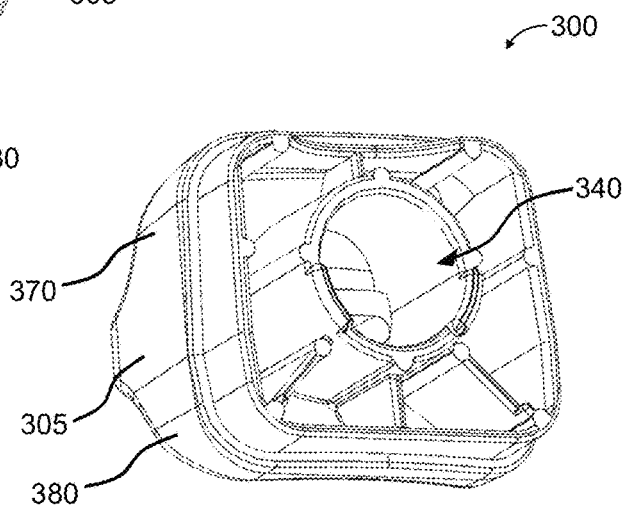
Figure 10E:
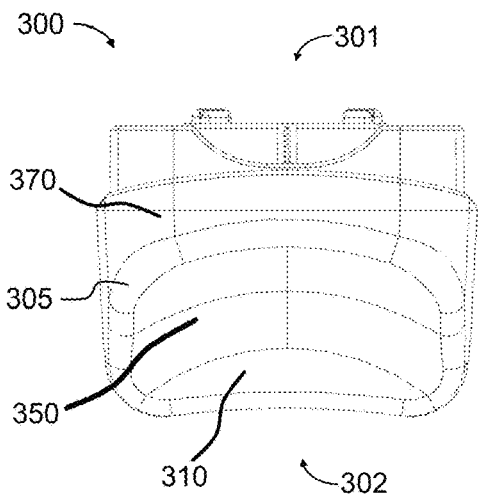
Figure 10F:
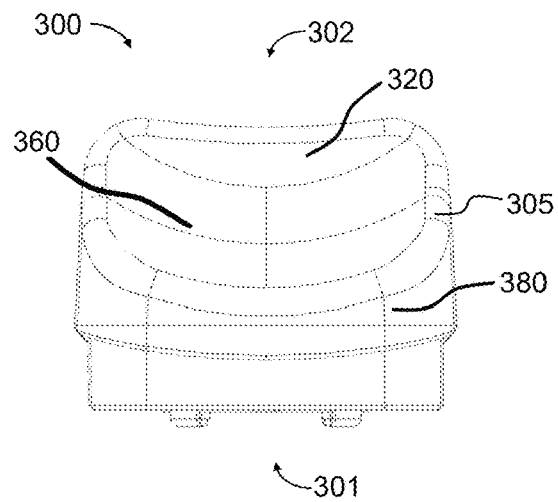
Figure 10G:
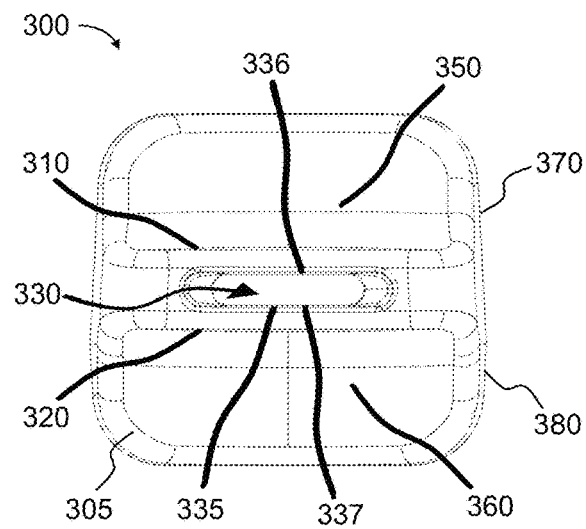
Figure 10H:
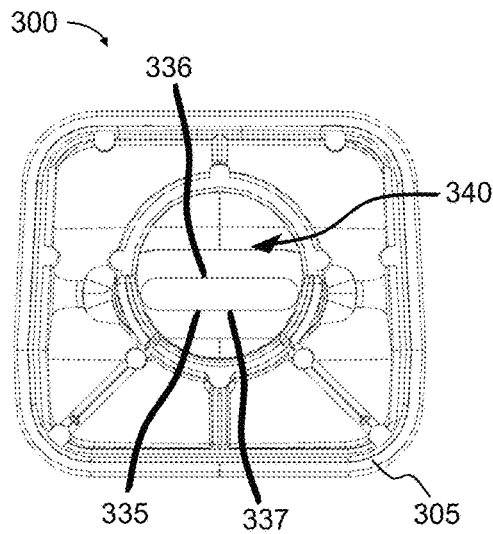
Figure 10I:
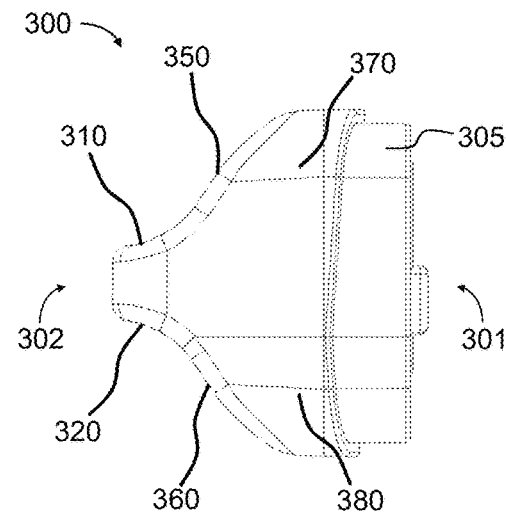
Figure 10J:
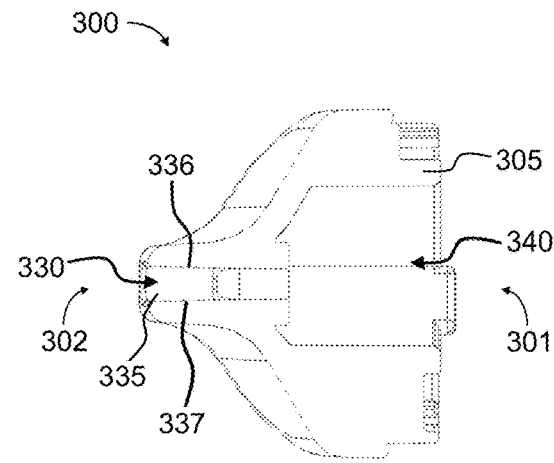

FIGS. 10A-10J show various views of an embodiment of a mouthpiece 300 of a breath analysis device. FIG. 10A shows a proximal end top perspective view of an embodiment of a mouthpiece 300 of a breath analysis device. FIG. 10B shows a proximal end bottom perspective view of the mouthpiece 300 of FIG. 10A. FIG. 10C shows a distal end top perspective view of the mouthpiece 300 of FIG. 10A. FIG. 10D shows a distal end bottom perspective view of the mouthpiece 300 of FIG. 10A. FIG. 10E shows a top view of the mouthpiece 300 of a FIG. 10A. FIG. 10F shows a bottom view of the mouthpiece 300 of FIG. 10A. FIG. 10G shows a proximal end view of the mouthpiece 300 of FIG. 10A. FIG. 10H shows a distal end view of the mouthpiece 300 of FIG. 10A. FIG. 10I shows a side view of the mouthpiece 300 of FIG. 10A. FIG. 10J shows a cross-sectional side view of the mouthpiece 300 of FIG. 10A.

As shown through FIGS. 10A-10J, the mouthpiece 300 may comprise a mouthpiece body 305 with a proximal end 302, a distal end 301, a vertical height, a horizontal width, and a horizontal length. The mouthpiece body 305 may terminate at the proximal end 302 in an upper lip surface 310 and a lower lip surface 320. In some embodiments and as shown, the upper lip surface 310 and the lower lip surface 320 may extend generally horizontally across substantially the entire horizontal width of the mouthpiece body 305. In some embodiments and as shown, the vertical height between the upper lip surface 310 and the lower lip surface 320 may be less than the vertical height of the mouthpiece body 305 at the distal end 301. Also as shown through FIGS. 10A-10J, the mouthpiece 300 may comprise an inlet opening 330 at the proximal end 302 of the mouthpiece body 305, the inlet opening 330 having a vertical height and a horizontal width. In some embodiments, the horizontal width of the inlet opening 330 is greater than the vertical height. Further as shown through FIGS. 10A-10J, the mouthpiece 300 may comprise an outlet opening 340 within the mouthpiece body 305, the outlet opening 340 being in fluid communication with inlet opening 330 of the mouthpiece body 305. The mouthpiece outlet opening 340 may be in fluid communication with an internal passage and/or inner cavity of the breath analysis device 200 (e.g., the internal cavity of airbox 220).

In some embodiments and as shown through FIGS. 10A-10J, the mouthpiece body 305 of mouthpiece 300 may further comprise an upper transition surface 350 extending lengthwise from the upper lip surface 310 toward the distal end 301, and a lower transition surface 360 extending lengthwise from the lower lip surface 320 toward the distal end 301. In some embodiments, the upper transition surface 350 and the lower transition surface 360 may be partially vertically inclined and extend across substantially the entire width of the mouthpiece body 305. In some embodiments, the upper transition surface 350 and the lower transition surface 360 may comprise smooth, concave surfaces extending across substantially the entire width of the mouthpiece body 305.

In some embodiments and as shown through FIGS. 10A-10J, the upper transition surface 350 may face in a generally proximal and upward direction and the lower transition surface 360 may face in a generally proximal and downward direction. Further as shown, in some embodiments the mouthpiece body 305 may comprise upper side edges 370 partially surrounding the upper transition surface 350 and the upper lip surface 310 and lower side edges 380 partially surrounding the lower transition surface 360 and the lower lip surface 320.

In some embodiments and as shown through FIGS. 10A-10J, the mouthpiece body 305 may comprise a substantially constant width over substantially an entire length of the upper transition surface 350 and the lower transition surface 360.

In some embodiments and as shown through FIGS. 10A-10J, the upper transition surface 350 and the lower transition surface 360 of the mouthpiece body 305 may be partially vertically inclined at an angle of about 45 degrees. In some embodiments, the upper transition surface 350 and the lower transition surface 360 of the mouthpiece body 305 may be partially vertically inclined at an angle of between about 30 and about 90 degrees relative to a horizontal plane.

In some embodiments, the upper lip surface 310 and the lower lip surface 320 of the mouthpiece body 305 may be substantially smooth. In some embodiments, the upper lip surface 310 may have a generally crescent shape and the lower lip surface 320 may have a generally crescent shape.

In some embodiments and as shown through FIGS. 10A-10J, the inlet opening 330 of the mouthpiece body 305 may be positioned midway along the vertical height of the mouthpiece body 305. In some embodiments, the inlet opening 330 of the mouthpiece body 305 may be positioned above or below a midway point along the vertical height of the mouthpiece body 305. In some embodiments, the inlet opening 330 of the mouthpiece body 305 may comprise an obround shape. In some embodiments, the inlet opening 330 of the mouthpiece body 305 may comprise a rectangular shape, an oval shape, or a polygonal shape.

In some embodiments, the horizontal width of the inlet opening 330 may be about 0.72". In some embodiments, the horizontal width of the inlet opening 330 may be between about 0.70" and about 1.00". In some embodiments, the vertical height between the upper lip surface 310 and the lower lip surface 320 may be about 0.26". In some embodiments, the vertical height between the upper lip surface 310 and the lower lip surface 320 may be between about 0.19" and about 0.4". In some embodiments, the vertical height of the mouthpiece body 305 at the distal end 301 may be about 1.22". In some embodiments, the vertical height of the mouthpiece body 305 at the distal end 301 may be between about 0.88" and about 1.50". In some embodiments, the horizontal width of the mouthpiece body 305 from the distal end 301 and over substantially the entire length of the mouthpiece body 305 to the proximal end 302 may be about 1.37". In some embodiments, the horizontal width of the mouthpiece body 305 from the distal end 301 and over substantially the entire length of the mouthpiece body 305 to the proximal end 302 may be between about 0.88" and about 1.50". In some embodiments, the horizontal length of the mouthpiece body 305 may be about 1.06". In some embodiments, the horizontal length of the mouthpiece body 305 may be between about 0.63" and about 1.50". In some embodiments, the mouthpiece body 305 may comprise a generally trapezoidal transverse cross-sectional shape. In some embodiments, the inlet opening 330 may comprise an interior passage 335 having an upper interior surface 336 and a lower interior surface 337. In some embodiments, the upper interior surface 336 and the lower interior surface 337 of the interior passage 335 may be substantially parallel to the upper lip surface 310 and the lower lip surface 320, respectfully.

According to some embodiments, the features of the mouthpiece 300 described herein may facilitate a substantially air-tight seal between a user's mouth and the mouthpiece 300 when in use. In some embodiments, a substantially air-tight seal between a user's mouth and the mouthpiece 300 comprises a substantially air-tight seal between a user's mouth and the mouthpiece inlet opening 330. In some embodiments, a substantially air-tight seal between a user's mouth and the mouthpiece 300 comprises a substantially air-tight seal between a user's mouth and the mouthpiece inlet opening 330 that fluidly connects a user's mouth to the inlet opening 330. The various dimensions and features of embodiments of the mouthpiece 300 described herein may allow a user to blow into the mouthpiece 300 without a need (or without a substantial need) to utilize and/or activate muscles of the mouth to form a substantially air-tight seal when in use. For example, the upper transition surface 350 and the lower transition surface 360 may be pressed against the user's upper and lower lips, respectively, to form a substantially air-tight seal without the need for the user to utilize and/or activate muscles of their mouth. As another example, both the upper lip surface 310 and the upper transition surface 350 along with both the lower lip surface 320 and the lower transition surface 360 may be pressed against the user's upper and lower lips, respectively, to form a substantially air-tight seal without the need for the user to utilize and/or activate muscles of their mouth.

While embodiments of the breath sample device 200 illustrated in FIGS. 7A-9G are constructed of the mouthpiece 300 and a separate device housing 205, other embodiments may construct the mouthpiece 300 and the device housing 205 from a unitary structure, or from more than two separate structures. As shown in FIGS. 9E-9G, in some embodiments the mouthpiece 300 may be interference fit to the airbox 220 and form a substantially leak-free air seal. For embodiments wherein the mouthpiece 300 may by removably attachable to the breath sample device 200, distal components of the mouthpiece 300 may be lengthened to allow for a sealing member (e.g., an o-ring) to fit in the interface between the mouthpiece 300 and the airbox 220. Similarly, for embodiments wherein the mouthpiece 300 may by removably attachable to the breath sample device 200, a proximal end of the airbox 220 may be lengthened to allow for a sealing member (e.g., an o-ring) to fit in the interface between the mouthpiece 300 and the airbox 220. In some embodiments wherein the mouthpiece 300 may by removably attachable to the breath sample device 200, distal components of the mouthpiece 300 that interact with the airbox 220 may increase in diameter to allow for a sealing member (e.g., an o-ring) to fit between the mouthpiece 300 and the airbox 220 to form a substantially air-tight seal. In some embodiments wherein the mouthpiece 300 may by removably attachable to the breath sample device 200, the proximal end of the airbox 220 that interact with the distal end of the mouthpiece 300 may decrease in diameter to allow for a sealing member (e.g., an o-ring) to fit between the mouthpiece 300 and the airbox 220 to form a substantially air-tight seal. In some embodiments wherein the mouthpiece 300 may by removably attachable to the breath sample device 200, distal components of the mouthpiece 300 that interact with the airbox 220 may decrease in diameter to allow for a sealing member (e.g., an o-ring) to fit between the mouthpiece 300 and the airbox 220 to form a substantially air-tight seal. In some embodiments wherein the mouthpiece 300 may by removably attachable to the breath sample device 200, the proximal end of the airbox 220 that interact with the distal end of the mouthpiece 300 may increase in diameter to allow for a sealing member (e.g., an o-ring) to fit between the mouthpiece 300 and the airbox 220 to form a substantially air-tight seal. In some embodiments, a removably attachable mouthpiece 300 may facilitate cleanliness, hygiene, and a change of filter 210 for a user of the breath sample device 200 and/or allow for cleaning of the mouthpiece 300 and a change of filter 210 between different users.

In some embodiments, a sample fluid may enter the breath analysis device 200 through the mouthpiece inlet opening 330, travel distally through the mouthpiece interior passage 335, through the mouthpiece outlet opening 340, through the filter 210, through the airbox 220, past the main PCB 208 and the airbox gasket 227, through the sled 230, through the cartridge gasket 235, through the breath sample analysis capture cartridge 100 as described herein, and out vent 255.

The breath analysis device 200 may be a portable, small, and hand-held device. In some embodiments, the breath analysis device 200 may have a length from the proximal end of the mouthpiece body 305 to the distal end of the housing 205 inclusive of the power switch 290 of about 6.04". In some embodiments, the breath analysis device 200 may have a length from the proximal end of the mouthpiece body 305 to the distal end of the housing 205 inclusive of the power switch 290 of between about 4" and about 8". In some embodiments, the breath analysis device 200 may have a vertical height inclusive of slider 270 and slider button 275 of about 1.32". In some embodiments, the breath analysis device 200 may have a vertical height inclusive of slider 270 and slider button 275 between about 0.8" and 2". In some embodiments, the breath analysis device 200 may have a horizontal width of about 1.37". In some embodiments, the breath analysis device 200 may have a horizontal width of between about 0.8" and 2". In some embodiments, the breath analysis device 200 housing 205 may comprise a generally trapezoidal transverse cross-sectional shape.

Methods of Performing a Breath Analysis

A method of performing a breath analysis by a user may comprise: powering on the breath analysis device 200 using the power switch 290; sliding the slider 270 proximally to cause the slideable door 250 to open and expose the cradle 245; installing the breath sample capture cartridge 100 into the breath analysis device 200 through the cartridge insertion window 245 and onto the cradle 245; sliding the slider 270 distally to cause the slideable door 250 to close; blowing into the mouthpiece 300; pushing the slider button 275 inward; sliding the slider 270 distally while pushing the slider button 275 inward; sliding the slider 270 proximally to open the slideable door 250; removing the breath sample capture cartridge 100; sliding the slider 270 distally to cause the slideable door 250 to close; and powering off the breath analysis device 200 using the power switch 290. In some embodiments, the method may include the breath analysis device 200 communicating with an application on another electronic device, such as a phone. In some embodiments, the method may include the breath analysis device 200 communicating with an application on another electronic device, such as a phone, with the another electronic device performing and reporting the breath sample analysis.

In some embodiments, to perform a breath analysis a user may use the breath sample device 200 in combination with another electronic device, such as a phone. In some embodiments, the another electronic device may have an application used for guiding, analyzing, and/or reporting the breath analysis. In some embodiments, the another electronic device may have an application used for providing various instructions at various stages of use of the breath analysis device 200. In some embodiments, a method to perform a breath analysis using the breath sample device 200 and the breath sample capture cartridge 100 as described herein comprises: powering on the breath analysis device 200 using the power switch 290; opening the application and wirelessly connecting the breath analysis device 200 to the application; sliding the slider 270 proximally causing the slideable door 250 to open and reveal the cartridge insertion window 240 and the cradle 245; installing the breath sample capture cartridge 100 into the breath analysis device 200 through the cartridge insertion window 245 and onto the cradle 245 with the lens cap 110 oriented distally; sliding the slider 270 distally to cause the slideable door 250 to close, which may cause the breath analysis device 200 to communicate with the application to check that the breath sample capture cartridge 100 is new/unused; blowing into the mouthpiece 300 of the breath analysis device 200, which may comprise the breath/fluid sample flowing through the breath analysis device 200 and into the breath sample capture cartridge 100 and causing the breath/fluid sample to interact with the interactant 120, and which may also comprise first blowing for about three seconds not into the mouthpiece 300 then continuing to blow out to finish the breath/exhale into the mouthpiece 300 until the breath analysis device 200 makes an indication to the user, such as an audible beep or tone and/or flash or flashes of light, once a volume threshold has been met (this method may allow for the capture of a lower lung sample and/or alveolar breath/air sample); pushing the slider button 275 inward and while holding inward sliding the slider 270 distally, which may cause the developer solution 175 to interact with the interactant 120 within the breath sample capture cartridge 100; allowing the application to communicate with the breath analysis device 200 and perform the breath analysis with the breath analysis device 200; sliding the slider 270 proximally to cause the slideable door 250 to open; removing the used breath capture sample cartridge 100; sliding the slider 270 distally to cause the slideable door 250 to close; receiving analysis results from the application; and powering off the breath analysis device 200 using the power switch 290.

The breath analysis process may include the use of a sensor, which may comprise LEDs 263 and detector 265 (e.g., a photodiode) within the breath analysis device 200 for measuring a color change, or other optical change, produced by a chemical reaction within the breath capture sample cartridge 100. In some embodiments, the LEDs 263 of the sensor may illuminate the interactant 120 within the breath capture sample cartridge 100 through the lens 112, and the detector 265 may measure a color or intensity change produced by the chemical reaction of the interactant 120 with the developer solution 175 after the user's breath/fluid sample passes through the breath capture sample cartridge 100. For example, in the case of acetone, acetone in the user's breath/fluid sample may be absorbed by the interactant 120 in the breath capture sample cartridge 100, and upon the chemical reaction between the interactant 120 and the developer solution 175, a color change may be caused that can be sensed. The magnitude of this color change may be dependent upon the quantity of acetone absorbed by the interactant 120.

In some embodiments, LEDs 263 of the breath analysis device may serve a dual purpose, that is, they may be used as a sensor and for providing visual indications to a user. In some embodiments, visual indications may include feedback to a user indicating certain actions may need to be performed and/or are completed (e.g., a breath analysis is complete). In some embodiments, such dual-use LEDs may illuminate components of the breath analysis device 200 and/or breath sample capture cartridge 100 that are transparent or translucent. In some embodiments, components of the breath analysis device 200 that are transparent or translucent may include the slideable door 250, the power switch 290, the mouthpiece 300, and the slider button 275. In some embodiments, multiple components of the breath sample capture cartridge 100 may be transparent or translucent.

The foregoing description and examples has been set forth merely to illustrate the disclosure and are not intended as being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure. Furthermore, all references cited herein are incorporated by reference in their entirety.

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Where term "about" is utilized before a range of two numerical values, this is intended to include a range between about the first value and about the second value, as well as a range from the first value specified to the second value specified.

Unless otherwise explicitly stated, articles such as "a" or "an" should generally be interpreted to include one or more described items. Accordingly, phrases such as "a device configured to" are intended to include one or more recited devices. Such one or more recited devices can be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

Although systems, devices, components, and methods for breath collection, sampling, segmentation, and analysis have been disclosed in the context of certain embodiments and examples, this disclosure extends beyond the specifically disclosed embodiments to other alternative embodiments and/or uses of the embodiments and certain modifications and equivalents thereof. Various features and aspects of the disclosed embodiments can be combined with or substituted for one another in order to form varying modes of systems and methods for breath collection, sampling, segmentation, and analysis. The scope of this disclosure should not be limited by the particular disclosed embodiments described herein.

Certain features that are described in this disclosure in the context of separate implementations can be implemented in combination in a single implementation. Conversely, various features that are described in the context of a single implementation can be implemented in multiple implementations separately or in any suitable subcombination. Although features may be described herein as acting in certain combinations, one or more features from a claimed combination can, in some cases, be excised from the combination, and the combination may be claimed as any subcombination or variation of any subcombination.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Further, the disclosure herein of any particular feature, aspect, method, property, characteristic, quality, attribute, element, or the like in connection with an embodiment can be used in all other embodiments set forth herein. Any methods disclosed herein need not be performed in the order recited. Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some embodiments, acts or events can be performed concurrently, e.g., through multi-threaded processing, interrupt processing, or multiple processors or processor cores or on other parallel architectures, rather than sequentially. Further, no element, feature, block, or step, or group of elements, features, blocks, or steps, are necessary or indispensable to each embodiment. Additionally, all possible combinations, subcombinations, and rearrangements of systems, methods, features, elements, modules, blocks, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some embodiments may be performed using the sequence of operations described herein, while other embodiments may be performed following a different sequence of operations.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described herein should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying figures. Certain figures are drawn and/or shown to scale, but such scale should not be limiting, since dimensions and proportions other than what are shown are contemplated and are within the scope of the embodiments disclosed herein. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

The methods disclosed herein may include certain actions taken by a practitioner; however, the methods can also include any third-party instruction of those actions, either expressly or by implication. For example, actions such as "positioning an electrode" include "instructing positioning of an electrode."

In summary, various embodiments and examples of systems and methods for breath collection, sampling, segmentation, and analysis have been disclosed. Although the systems and methods for breath collection, sampling, segmentation, and analysis have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Thus, the scope of this disclosure should not be limited by the particular disclosed embodiments described herein, but should be determined only by a fair reading of the claims that follow.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 V" includes "1 V." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure.

The invention claimed is:

1. A breath analysis device, comprising:
   a breath sample collection body comprising a housing and an internal passage configured to route a breath sample within the housing for collection and/or analysis of a breath analyte; and
   a mouthpiece body having: a proximal end, a distal end, a vertical height, a horizontal width and a horizontal length, wherein the mouthpiece body terminates at the proximal end in an upper lip surface and a lower lip surface, wherein the upper lip surface and the lower lip surface comprise generally planar surfaces that extend generally horizontally across substantially the entire horizontal width of the mouthpiece body, wherein the vertical height between the upper and lower lip surfaces is less than the vertical height of the mouthpiece body at the distal end, wherein a horizontal center of the upper and lower lip surfaces with respect to the horizontal width extends farther distal than adjacent horizontal side portions of the upper and lower lip surfaces that taper in the proximal direction, wherein the mouthpiece body further comprises an upper transition surface extending lengthwise from the upper lip surface toward the distal end and a lower transition surface extending lengthwise from the lower lip surface toward the distal end, the upper and lower transition surfaces being partially vertically inclined and having smooth, concave surfaces, wherein the upper lip surface and the lower lip surface are configured to contact an upper lip and a lower lip of a user, respectively, during exhalation, and wherein the upper transition surface and the lower transition surface are configured to contact the upper lip and the lower lip of the user, respectively, during exhalation; an inlet opening at the proximal end of the mouthpiece body, the inlet opening having a vertical height and a horizontal width, wherein the horizontal width is greater than the vertical height; and an outlet opening within the mouthpiece body, the outlet opening being in fluid communication with the internal passage of the breath sample collection body.

2. The breath analysis device of claim 1, wherein the smooth, concave surfaces of the upper and lower transition surfaces extend across substantially the entire width of the mouthpiece body.

3. The breath analysis device of claim 1, wherein the upper transition surface faces in a generally proximal and upward direction and the lower transition surface faces in a generally proximal and downward direction.

4. The breath analysis device of claim 1, wherein the mouthpiece body further comprises upper side edges partially surrounding the upper transition surface and the upper lip surface and lower side edges partially surrounding the lower transition surface and the lower lip surface.

5. The breath analysis device of claim 1, wherein the mouthpiece body has a substantially constant width over substantially an entire length of the upper and lower transition surfaces.

6. The breath analysis device of claim 1, wherein the upper and lower transition surfaces are partially vertically inclined at an angle between 30 and 90 degrees relative to a horizontal plane.

7. The breath analysis device of claim 1, wherein the mouthpiece body is integrally formed with the housing.

8. The breath analysis device of claim 1, wherein the mouthpiece body is removably attachable to the housing.

9. The breath analysis device of claim 1, wherein the upper lip surface and the lower lip surface are substantially smooth.

10. The breath analysis device of claim 1, wherein the upper lip surface has a generally crescent shape and the lower lip surface has a generally crescent shape.

11. The breath analysis device of claim 1, wherein the inlet opening is positioned midway along the vertical height of the mouthpiece body.

12. The breath analysis device of claim 1, wherein the inlet opening has an obround shape.

13. The breath analysis device of claim 1, wherein the horizontal width of the inlet opening is between 0.75" and 1.00".

14. The breath analysis device of claim 1, wherein the vertical height between the upper and lower lip surfaces is between 0.19" and 0.4".

15. The breath analysis device of claim 1, wherein the vertical height of the mouthpiece body at the distal end is between 0.8" and 1.50".

16. The breath analysis device of claim 1, wherein the horizontal width of the mouthpiece body from the distal end and over substantially the entire length of the mouthpiece body to the proximal end is between 0.88" and 1.50".

17. The breath analysis device of claim 1, wherein the horizontal length of the mouthpiece body is between 0.63" and 1.50".

18. The breath analysis device of claim 1, wherein the mouthpiece body has a generally trapezoidal transverse cross-sectional shape.

19. The breath analysis device of claim 1, wherein the inlet opening comprises an interior passage having an upper interior surface and a lower interior surface that are substantially parallel to the upper lip surface and the lower lip surface, respectively.

20. The breath analysis device of claim 1, wherein the upper lip surface is configured to form a substantially air-tight seal with the upper lip of the user during exhalation, and the lower lip surface is configured to form a substantially air-tight seal with the lower lip of the user during exhalation.

21. The breath analysis device of claim 1, wherein the upper transition surface is configured to form a substantially air-tight seal with the upper lip of the user during exhalation, and the lower transition surface is configured to form a substantially air-tight seal with the lower lip of the user during exhalation.

22. The breath analysis device of claim 1, wherein a flow path of the breath analysis device produces a non-trivial amount of flow resistance.

23. The breath analysis device of claim 1, further comprising a breath sample capture cartridge in a flow path of the breath analysis device, the breath sample capture cartridge configured to collect the breath analyte and producing a non-trivial amount of flow resistance.

24. A mouthpiece for a breath analysis device having a non-trivial amount of flow resistance, the mouthpiece comprising:
- a mouthpiece body having a proximal end, a distal end, a vertical height, a horizontal width and a horizontal length, the mouthpiece body comprising:
  - an upper lip surface and a lower lip surface at the proximal end, the upper lip surface and the lower lip surface comprising generally planar surfaces extending generally horizontally across the horizontal width of the mouthpiece body, wherein a horizontal center of the upper and lower lip surfaces with respect to the horizontal width extends farther distal than adjacent horizontal side portions of the upper and lower lip surfaces that taper in the proximal direction, and wherein the upper lip surface and the lower lip surface are configured to contact an upper lip and a lower lip of a user, respectively, during exhalation;
  - an upper transition surface extending lengthwise from the upper lip surface toward the distal end and a lower transition surface extending lengthwise from the lower lip surface toward the distal end, the upper and lower transition surfaces having smooth, concave surfaces, wherein the upper transition surface and the lower transition surface are configured to contact the upper lip and the lower lip of the user, respectively, during exhalation;
  - an inlet opening at the proximal end, the inlet opening having a vertical height and a horizontal width, the horizontal width of the inlet opening being greater than the vertical height of the inlet opening; and
  - an outlet opening within the mouthpiece body, the outlet opening configured to be in fluid communication with an internal passage of the breath analysis device.

25. The mouthpiece of claim 24, wherein the vertical height between the upper and lower lip surfaces is less than the vertical height of the mouthpiece body at the distal end.

26. The mouthpiece of claim 24, wherein the mouthpiece body has a substantially constant width over substantially an entire length of the upper and lower transition surfaces.

27. The mouthpiece of claim 24, wherein the mouthpiece body further comprises upper side edges partially surrounding the upper transition surface and the upper lip surface and lower side edges partially surrounding the lower transition surface and the lower lip surface.

28. The mouthpiece of claim 24, wherein the upper and lower transition surfaces are partially vertically inclined at an angle between 30 and 90 degrees relative to a horizontal plane.

29. The mouthpiece of claim 24, wherein the upper lip surface is configured to form a substantially air-tight seal with the upper lip of the user during exhalation, and the lower lip surface is configured to form a substantially air-tight seal with the lower lip of the user during exhalation.

30. The mouthpiece of claim 24, wherein the upper transition surface is configured to form a substantially air-tight seal with the upper lip of the user during exhalation, and the lower transition surface is configured to form a substantially air-tight seal with the lower lip of the user during exhalation.

* * * * *